(12) United States Patent
Cho et al.

(10) Patent No.: US 6,459,092 B2
(45) Date of Patent: Oct. 1, 2002

(54) 6 DEGREE-OF-FREEDOM (DOF) MOTION MEASURING APPARATUS

(75) Inventors: Hyung-suck Cho, Yuseong-gu Daejeon (KR); Won-shik Park, Seoul (KR); Kuk-won Ko, Seoul (KR); Noh-yeol Park, Seoul (KR); Yong-kyu Byun, Kiheung-eub Yongin (KR)

(73) Assignees: Korean Advanced Institute of Science & Technology (KR); Samsung Electronics Co., Ltd. (KR)

( * ) Notice: Subject to any disclaimer, the term of this patent is extended or adjusted under 35 U.S.C. 154(b) by 0 days.

(21) Appl. No.: 09/851,141

(22) Filed: May 9, 2001

(30) Foreign Application Priority Data

May 9, 2000 (KR) ........................................ 2000-24653
May 9, 2000 (KR) ........................................ 2000-24654

(51) Int. Cl.⁷ ......................... G01N 21/86; G01N 21/88; G01V 8/00
(52) U.S. Cl. ................... 250/559.37; 365/375; 702/153
(58) Field of Search ................. 250/559.29, 559.37, 250/559.31, 559.46; 365/375, 139.1; 702/153, 152, 151, 150

(56) References Cited

U.S. PATENT DOCUMENTS 5,510,892 A * 4/1996 Mizutani et al. ........ 250/559.37
5,884,239 A 3/1999 Romanik Jr.

OTHER PUBLICATIONS

Neville K. S. Lee et al., "High–Resolution Multidimensional Displacement Monitoring System", Optical Engineering, vol. 36, No. 8, pp. 2287–2293 (1997).

* cited by examiner

Primary Examiner—Hung Xuan Dang
(74) Attorney, Agent, or Firm—Burns, Doane, Swecker & Mathis, LLP

(57) ABSTRACT

A 6 degree-of-freedom (DOF) motion measuring apparatus using a multidirectional reflector, and a swing arm type optical system using the 6-DOF motion measuring apparatus to measure the 6-DOF motion of a slider in a hard disc drive (HDD) are provided. The 6-DOF motion measuring apparatus includes: a multidirectional reflector having at least three reflecting sides by which the laser beam is slit and reflected in three directions, the multidirectional reflector being provided to the object whose motion is to be measured; three position-sensitive detectors for receiving three sub-laser beams reflected from the multidirectional reflector; and a controller for calculating the 6-DOF motion of the multidirectional reflector using the intensity distributions of the three sub-laser beams received by the three position sensitive detectors assuming that the laser beam before reflection has a Gaussian intensity distribution. The 6-DOF motion of an object can be easily and precisely measured using the multidirectional reflector having three reflecting sides. The 6-DOF motion measuring apparatus can be applied to measure the displacement of a small object moving at high speed.

17 Claims, 19 Drawing Sheets

6 DEGREE-OF-FREEDOM (DOF) MOTION MEASURING APPARATUS

This application claims priority under 35 U.S.C. §§ 119 and/or 365 to Applications 00-24653 and 00-24654 filed in Republic of Korea on May 9, 2000; the entire content of which is hereby incorporated by reference.

BACKGROUND OF THE INVENTION

1. Field of the Invention

The present invention relates to a six degree-of-freedom (DOF) motion measuring apparatus, and more particularly, to a swing arm type optical system using the 6-DOF measuring apparatus to measure the motion of a slider in a hard disk drive (HDD).

2. Description of the Related Art

The position and orientation of an object (rigid body) in 3-dimensional (3-D) space can be measured by a variety of methods. As one of the methods extensively used, the position of an object is expressed as position vector in an orthogonal coordinate system, and the orientation of the object is expressed using Euler angles. The Euler angles are angles of rotation of an object about x, y, and z axes of the reference coordinate system, are referred to as rolling, pitching, and yawing angles, and are denoted by $\gamma$, $\beta$, and $\alpha$, respectively.

FIG. 1 illustrates the concept of 6-DOF motion and symbols used for describing the motion. As shown in FIG. 1, coordinate system $O_w$ is a reference coordinate system used to express motion of an object 1. Coordinate systems $O_w$, and $O_s$ are defined on object 1. Coordinate system $O_s$ is fixed to and moves along with object 1. Coordinate system $O_w$, has the same orientation as reference coordinate system $O_w$ and the same origin as coordinate system $O_s$. The position of object 1 in coordinate system $O_s$, is expressed by position vector $\vec{t}^w = [t_x \ t_y \ t_z]^T$. $T_s^w$ is a matrix having elements which include the parameters $t_x$, $t_y$, $t_z$, $\gamma$, $\beta$, and $\alpha$, as below, and $T_s^w$ defines the position and orientation of object 1 in coordinate system $O_s$ with respect to the reference coordinate system $O_w$:

$$T_s^w = \begin{bmatrix} c\alpha c\beta & c\alpha s\beta s\gamma - s\alpha c\gamma & c\alpha s\beta c\gamma + s\alpha s\gamma & t_x \\ s\alpha c\beta & s\alpha s\beta s\gamma + c\alpha c\gamma & s\alpha s\beta c\gamma - c\alpha s\gamma & t_y \\ -s\beta & c\beta s\lambda & c\beta c\gamma & t_z \\ 0 & 0 & 0 & 1 \end{bmatrix} \quad (1)$$

where c and s denote cosine and sine, respectively.

The coordinate system $O_s$ is fixed to object 1, and the position and orientation of object 1 are expressed using $T_s^w$. To calculate the values of the six elements $t_x$, $t_y$, $t_z$, $\gamma$, $\beta$, and $\alpha$ is to measure the position and orientation of object 1 in 3-D space.

According to conventional methods used to measure the position and orientation of object 1, multiple degree-of-freedom displacement is measured using sensors mounted on each axis of coordinate system.

FIG. 2 illustrates the concept of measuring the coordinates and orientation of an object in a 2-D plane using conventional capacitance-type proximity sensors. As shown in FIG. 2, signals from x1 and y1 proximity sensors 21 and 25 are used to measure displacement in x- and y-axial directions. An x2 proximity sensor 23 is installed parallel to the x1 proximity sensor 21 to measure the angle of rotation. However, to measure 6-DOF motion in 3-D space, two proximity sensors are required for each direction. Thus, to measure 6-DOF displacement using the conventional method, a plurality sensors are needed for each axis, which causes many difficulties in actual applications. Also, when such capacitance-type proximity sensors are used, the material of object 1 to be measured is limited to metal. In addition, installation of the sensors may be difficult depending on the shape of object 1. A small space must be maintained between object 1 and the proximity sensors 21, 23, and 25.

On the other hand, a Mikelson interferometer can be used as an apparatus for measuring 6-DOF motion of an object. FIG. 3 illustrates the structure of a conventional Mikelson interferometer applied to measure one-dimensional displacement. As shown in FIG. 3, a laser source 30, a beam splitter 32, and a cube corner reflector 34 are fixed in position, and another cube corner reflector 36 is affixed to the surface of object 1 whose motion is to be measured, so that optical paths are formed, as shown in FIG. 3. This complex configuration is for measuring one-dimensional displacement, and six such interferometers must be used to measure 6-DOF displacement. In addition to a configuration of six interferometers being significantly complicated, it is difficult to keep the optical path of each interferometer aligned for 6-DOF displacement.

FIG. 4 illustrates the concept of measuring 6-DOF motion of an object by conventional four position-sensitive detectors (PSDs). The 6-DOF displacement measuring system of FIG. 4, which is suggested in an article in *Optical Engineering*, Vol. 36, No. 8, pp. 2287–2293 (1997), includes four beam splitters 45, 46, 47, and 48, which are mounted on an object 1 whose motion is to be measured, four PSDs 41, 42, 43, and 44, and two lenses 49a and 49b. Transitions and rotations in three axial directions of the object 1 are measured by this system with a resolution of 0.05 $\mu$m and 0.25 $\mu$rad, respectively. The 6-DOF measuring system is advantageous in that 6-DOF transitional and rotational motions are simultaneously measured. However, the object 1 should be large enough such that four beam splitters 45, 46, 47, and 48 can be mounted thereon, and the 6-DOF measuring system is unsuitable for measuring high-speed motion.

FIG. 5 illustrates the concept of measuring 6-DOF displacement using a conventional apparatus in which a photodetector assembly is affixed to an object whose position and orientation are to be measured. The 6-DOF displacement measuring apparatus of FIG. 5 is disclosed in U.S. Pat. No. 5,884,239 by Romanik. As shown in FIG. 5, vertical and horizontal planar laser beams 56 are emitted from a scanner 56. The vertical planar laser beam scans in the horizontal direction and the horizontal planar laser beam scans in the vertical direction, so that a particular area within which the position and orientation of an object is to be measured is scanned with the laser beams. Four photodetectors 51, 52, 53, and 54 are given a particular 3-D arrangement defining a shape. As this photodetector assembly is scanned with the vertical and horizontal planar laser beams, each of the photodetectors 51, 52, 53, and 54 irradiated with the laser beams detects the intensity of the laser beams. The photodetectors 51, 52, 53, and 54 detect the laser beams in a particular order according to the shape, position, and orientation of the photodetector assembly. Since the shape of the photodetector assembly is constant, the position and orientation of the photodetector assembly can be measured by measuring the timing of detecting laser beams by each of the photodetectors 51, 52, 53, and 54. Based on this principle, the position and orientation of an object (not shown) can be measured by mounting such a photodetector assembly on the object. A single external photodetector 55, which is not one of the four photodetectors 51, 52, 53, and 54 which form the photodetector assembly, is used for synchronization between a scanning system and sensor signals.

To increase precision in the measurement of 6-DOF motion with the apparatus of FIG. 5, it is preferable to increase the size of the photodetector assembly. Thus, there is difficulty in measuring the motion of a small object with precision. In addition, the rate of obtaining measurement data is limited by the scanning speed of the scanning system, and thus the ability to measure the motion of an object that moves fast is limited by the scanning speed.

SUMMARY OF THE INVENTION

To solve the above problems of the conventional art, it is a first object of the present invention to provide an apparatus for measuring 6 degree-of-freedom (DOF) motion of an object, which can easily and precisely measure high-speed displacement of a small object using a multidirectional reflector.

It is a second object of the present invention to provide a structurally simple swing arm type optical system which uses the 6-DOF motion measuring apparatus to measure 6-DOF motion of a slider in a hard disc drive (HDD) and can accurately measure the dynamic characteristics of the slider in tracking and searching tracks.

To achieve the first object of the present invention, there is provided an apparatus for measuring 6 degree-of-freedom (DOF) motion of an object using a laser beam emitted from a laser source, the apparatus comprising: a multidirectional reflector having at least three reflecting sides by which the laser beam is slit and reflected in three directions, the multidirectional reflector being provided to the object whose motion is to be measured; three position-sensitive detectors for receiving three sub-laser beams reflected from the multidirectional reflector; and a controller for calculating the 6-DOF motion of the multidirectional reflector using the intensity distributions of the three sub-laser beams received by the three position sensitive detectors assuming that the laser beam before reflection has a Gaussian intensity distribution.

It is preferable that the laser beam from the laser source tracks the apex of the multidirectional reflector at which the three reflecting sides meet. It is preferable that the laser source can move in two dimensions such that the laser beam emitted from the laser source tracks the apex of the multidirectional reflector at which the three reflecting sides meet. It is preferable that the controller receives electric signals from the position-sensitive detectors, and analyzes the intensity distributions of the three sub-laser beams received by the position-sensitive detectors to determine whether or not the intensity distributions of the three sub-light beams are the same. It is preferable that the controller adjusts the location of the laser source if the intensity distributions of the three sub-light beams are not the same.

To achieve the second object of the present invention, there is provided a swing arm type optical system using a laser beam emitted from a laser beam scanner to measure 6 degree-of-freedom (DOF) motion of a slider in a hard disc drive (HDD), the swing arm type optical system comprising: a multidirectional reflector having three reflecting sides on which the laser beam is simultaneously incident, the multidirectional reflector being mounted on or adjacent to the slider, wherein the relative positions of the slider and the multidirectional reflector are fixed; at least one optical path forming reflector for adjusting the traveling path of the laser beam scanned from the laser beam scanner such that the laser beam is incident on the apex of the multidirectional reflector at which the three reflecting sides meet; three position-sensitive detectors disposed in the optical paths of three sub-laser beams reflected from the multidirectional reflector; a controller for measuring the 6-DOF motion of the multidirectional reflector by analyzing the intensity distributions of the three sub-laser beams received by the three position sensitive detectors assuming that the laser beam before reflection has a Gaussian intensity distribution; and a plurality of swing arms which support the slider and along which the traveling path of the laser beam is formed.

It is preferable that the rear ends of the plurality of the swing arms are connected to a pivot, and the plurality of swing arms pivot around the pivot. It is preferable that the plurality of swing arms comprise an upper swing arm and a lower swing arm, a through hole is formed at the front end of the upper swing arm, and the laser beam travels along the direction of the upper swing arm and is incident on the apex of the multidirectional reflector through the through hole.

It is preferable that the plurality of swing arms comprise an upper swing arm and a lower swing arm, the upper swing arm is formed as a rigid body, the lower swing arm includes a suspension and a flexure which are joined together, and the slider is mount on the bottom of the flexure.

It is preferable that the optical path forming reflector comprises a first reflector mounted on the top of the pivot about which the upper and lower swing arms pivot, and a second reflector mounted at the through hole of the upper swing arm; and the laser beam emitted from the laser beam scanner is reflected by the first and second reflectors and is incident on the apex of the multidirectional reflector.

It is preferable that the first and second reflectors have a 45-degree sloping side, the 45-degree sloping sides of the first and second reflectors face each other, the laser beam emitted from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

It is preferable that the first and second reflectors have a 45-degree sloping side, the 45-degree sloping sides of the first and second reflectors are parallel sloping down toward the front end of the upper swing arm, the laser beam scanned from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE INVENTION

Figure 1:
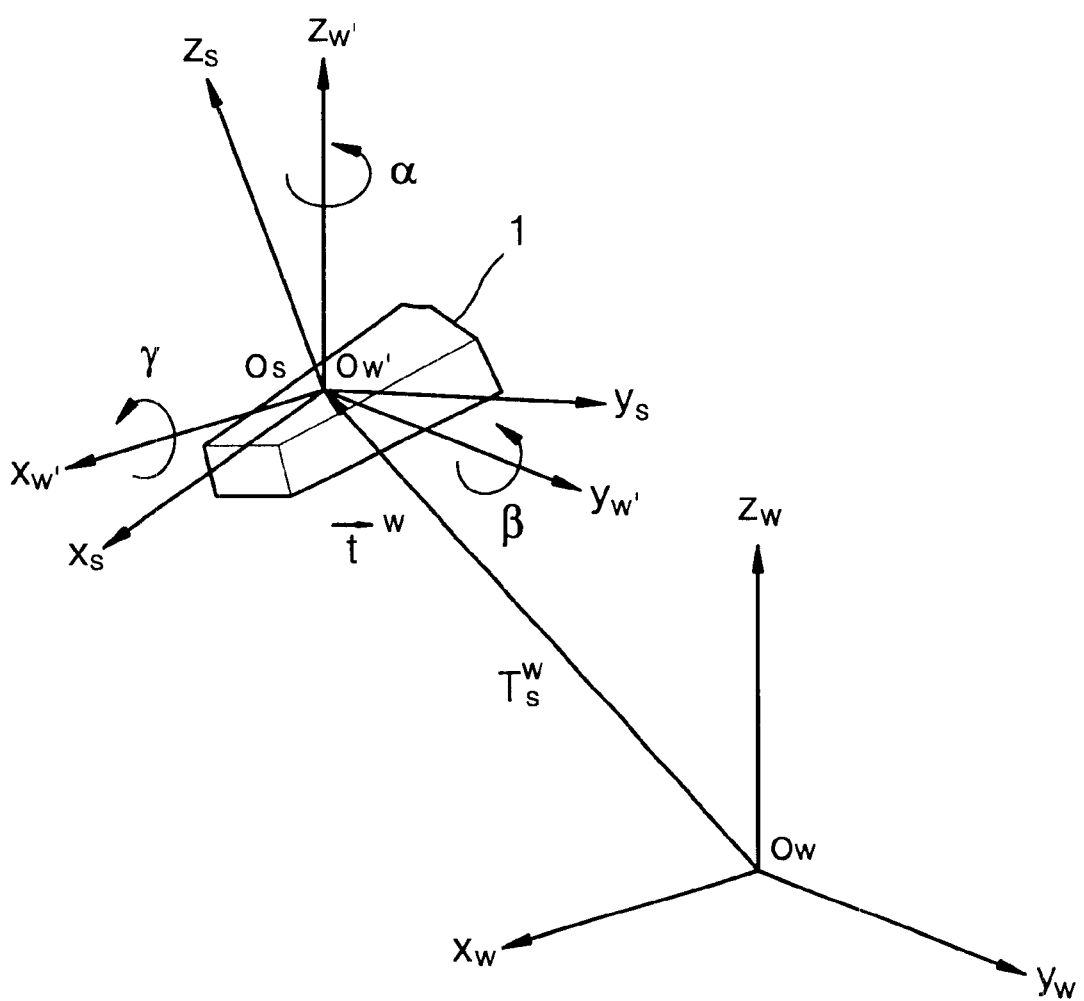
FIG. 1 illustrates the concept of 6-DOF motion and symbols used for describing the motion.
Figure 2:
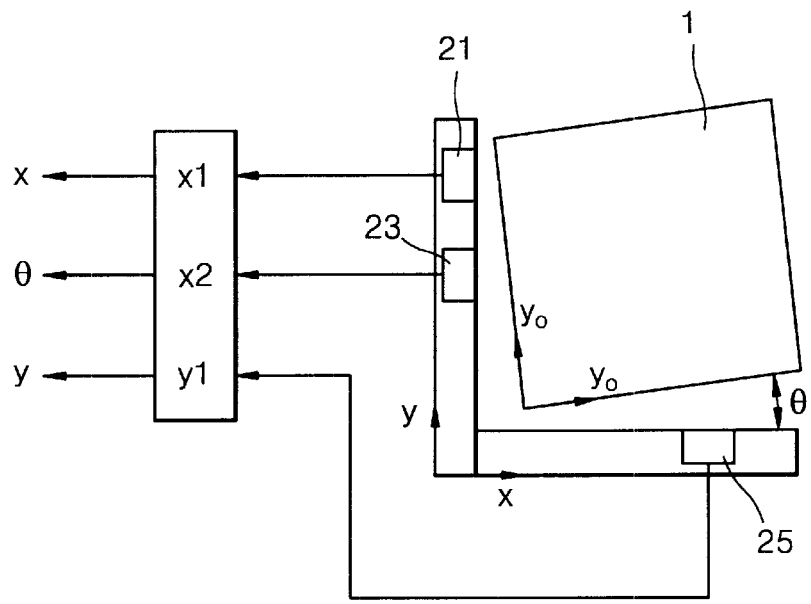
FIG. 2 illustrates the concept of measuring the coordinates and orientation of an object in a 2-dimensional (2-D) plane using conventional capacitance-type proximity sensors.
Figure 3:
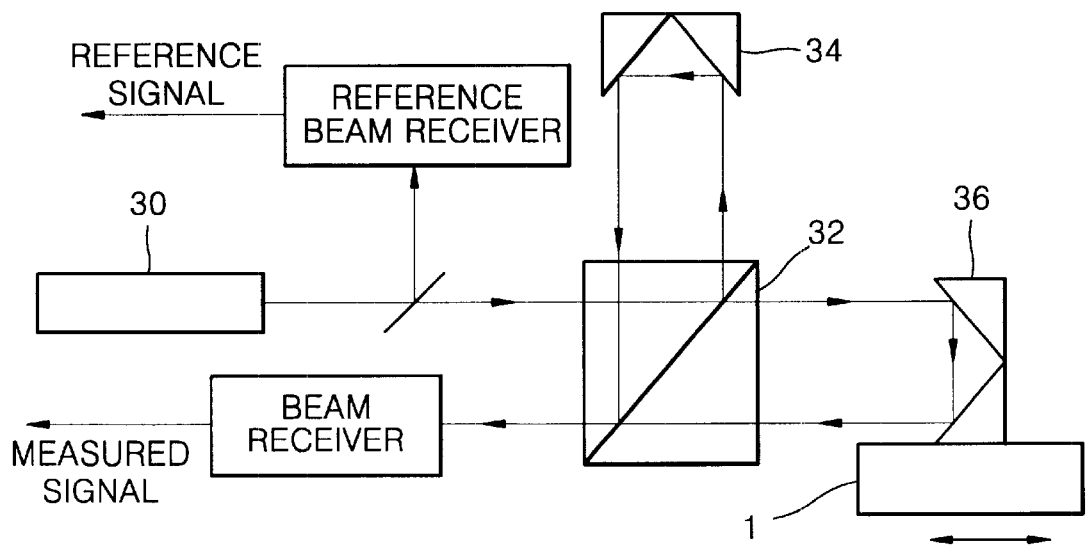
FIG. 3 illustrates the structure of a conventional Mikelson interferometer applied to measure uniaxial displacement.
Figure 4:
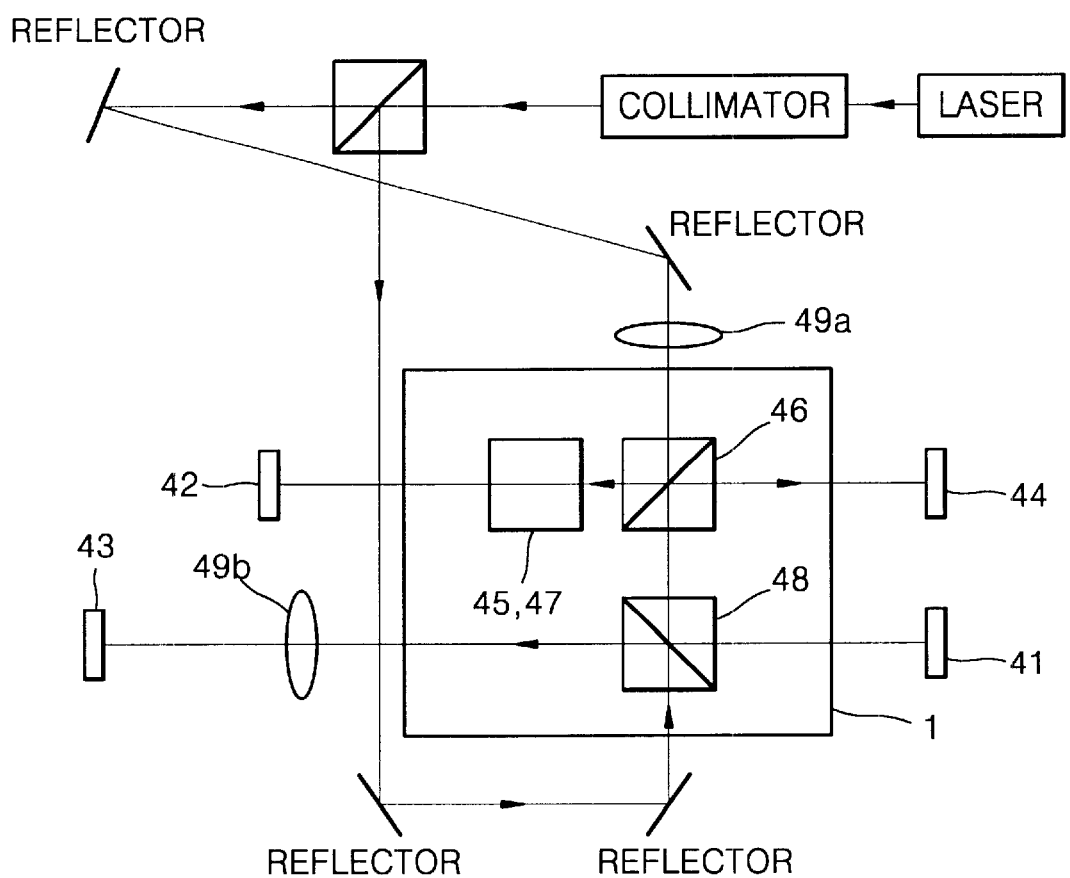
FIG. 4 illustrates the concept of measuring 6-DOF motion of an object using conventional four position-sensitive detectors (PSDs)
Figure 5:
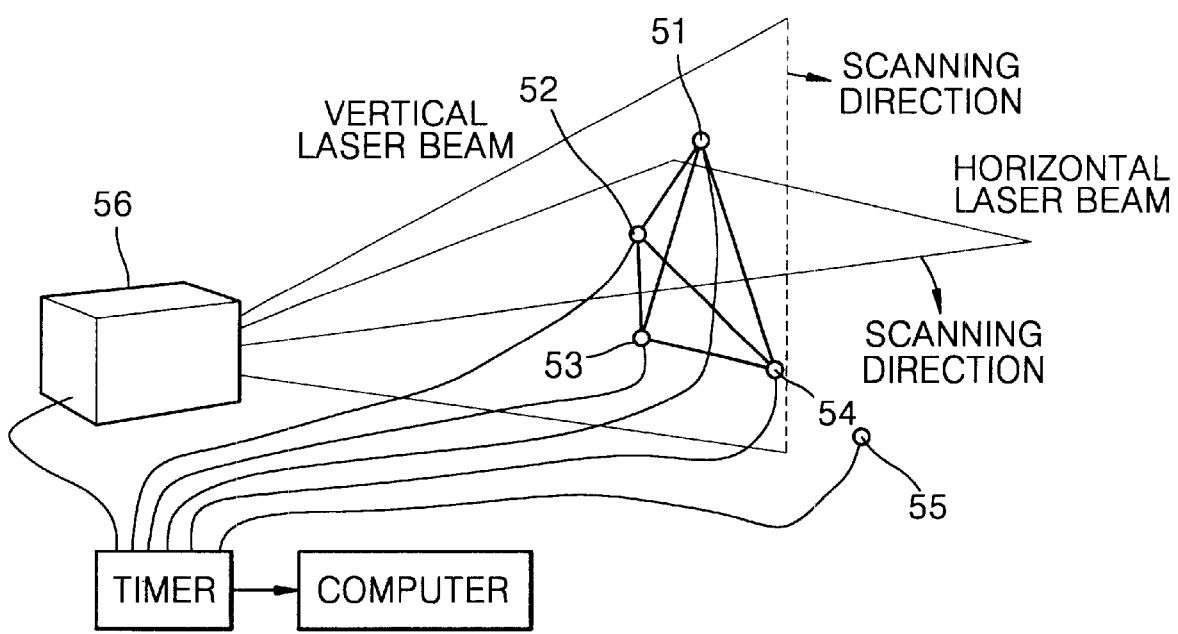
FIG. 5 illustrates the concept of measuring 6-DOF displacement using a conventional apparatus in which a photodetector assembly is affixed to an object whose motion is to be measured.
Figure 6:
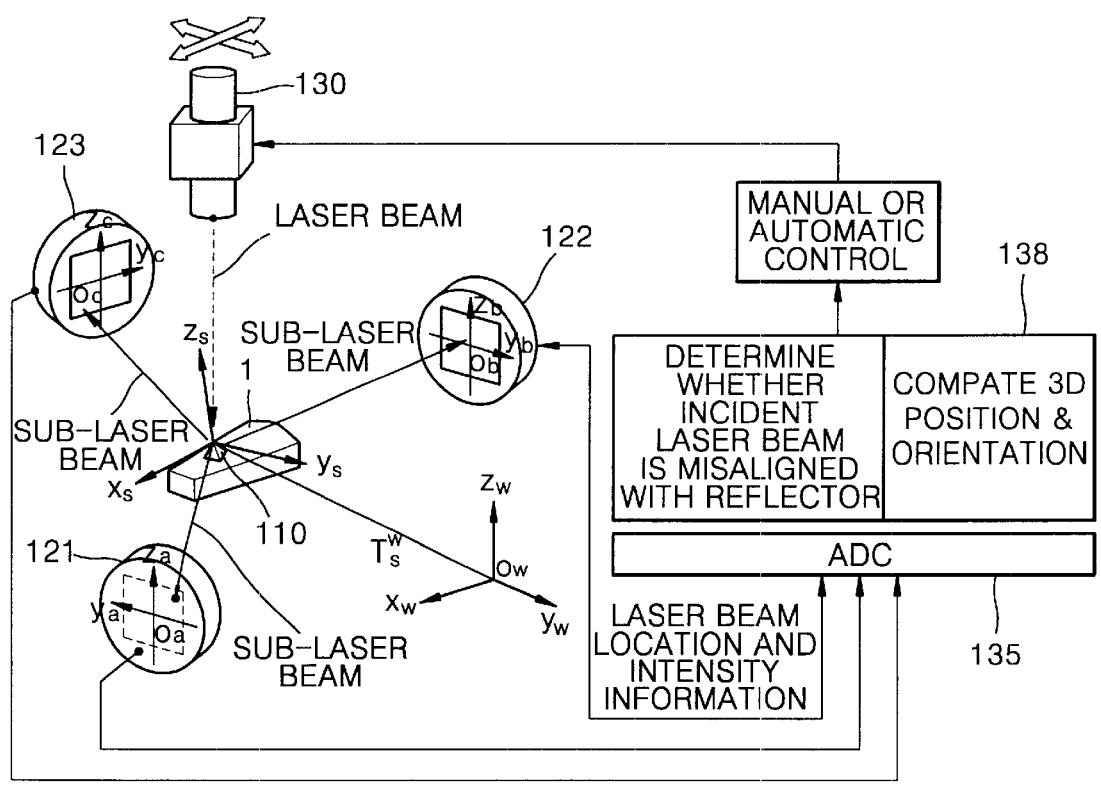
FIG. 6 illustrates the concept of a 6-DOF motion measuring apparatus using a multidirectional reflector according to a preferred embodiment of the present invention.

A preferred embodiment of a 6 degree-of-freedom (DOF) motion measuring apparatus using a multidirectional reflector, for example, a 3-facet mirror, according to the present invention is shown in FIG. 6. As shown in FIG. 6, a 3-facet reflector 110 in the form of a triangular pyramid shaped mirror, is mounted on an object 1 to be measured. The 3-facet reflector 110 as a tetrahedral mirror having three facets reflects a laser beam incident through the apex of the 3-facet reflector 110 into three sub-beams. The 3-facet reflector 110 is an example of the multidirectional reflector having at least three reflecting sides according to the present invention. In other words, according to the present invention, a multidirectional reflector having three or more reflecting sides can be used, and three of the sub-beams reflected from the reflector are used in measuring 6-DOF displacement of an object.

The multidirectional reflector or 3-facet reflector may be manufactured as a separate part, and then mounted on the object 1. The multidirectional reflector or 3-facet reflector may be formed as a single unit along with the object 1. Installation or shape of the multidirectional reflector or 3-facet reflector can be varied without limitation.

Three sub-laser beams reflected from the multidirectional reflector or 3-facet reflector, as described above, are detected by three position-sensitive detectors (PSDs) 121, 122, and 123. The PSDs 121, 122, and 123, which sense the intensity of incident laser beams and output electric signals, are formed of devices which are extensively used. 6-DOF displacement of the 3-facet reflector 110 is expressed as x-, y-, and z-coordinates, and rolling, pitching, and yawing angles and computed using three position coordinates on the three PSDs 121, 122, and 123. The 3-facet reflector 110 is attached to the object 1, and measures 6-DOF motion of the object 1 while moving along with the object 1. For accurate measurement results, the apex of the 3-facet reflector 110 must be aligned with the center of incident laser beam. Thus, the laser beam and the 3-facet reflector 110 must move together so that the laser beam tracks the apex of the 3-facet reflector 110. Adjusting the movement of the 3-facet reflector 110 and the location of a laser source 130 such that the center of the laser beam is kept aligned with the apex of the 3-facet reflector 110 will be described later in greater detail.

As shown in FIG. 6, three sub-laser beams reflected from the 3-facet reflector 110 are incident on the three PSDs 121, 122, and 123 and the 6-DOF displacement of the 3-facet reflector 110 is measured using information on the location and intensity of the sub-laser beams output from the PSDs 121, 122, and 123, and alignment between the incident laser beam and the apex of the 3-facet reflector 110 is adjusted. Here, signals output from the three PSDs 121, 122, and 123 are converted by an analog-to-digital converter (ADC) 135, and stored in a memory of a controller 138 for processing.

To measure the position and orientation of the 3-facet reflector 110 using the outputs from the three PSDs 121, 122, and 123, a mathematical relation between the 6-DOF displacement of the 3-facet reflector 110 and the outputs from the PSDs 121, 122, and 123 should be established. In the present invention, successive mathematical relations used to measure the 6-DOF displacement of the 3-facet reflector 110 using the outputs from the three PSDs 121, 122, and 123 are derived.

Figure 7:
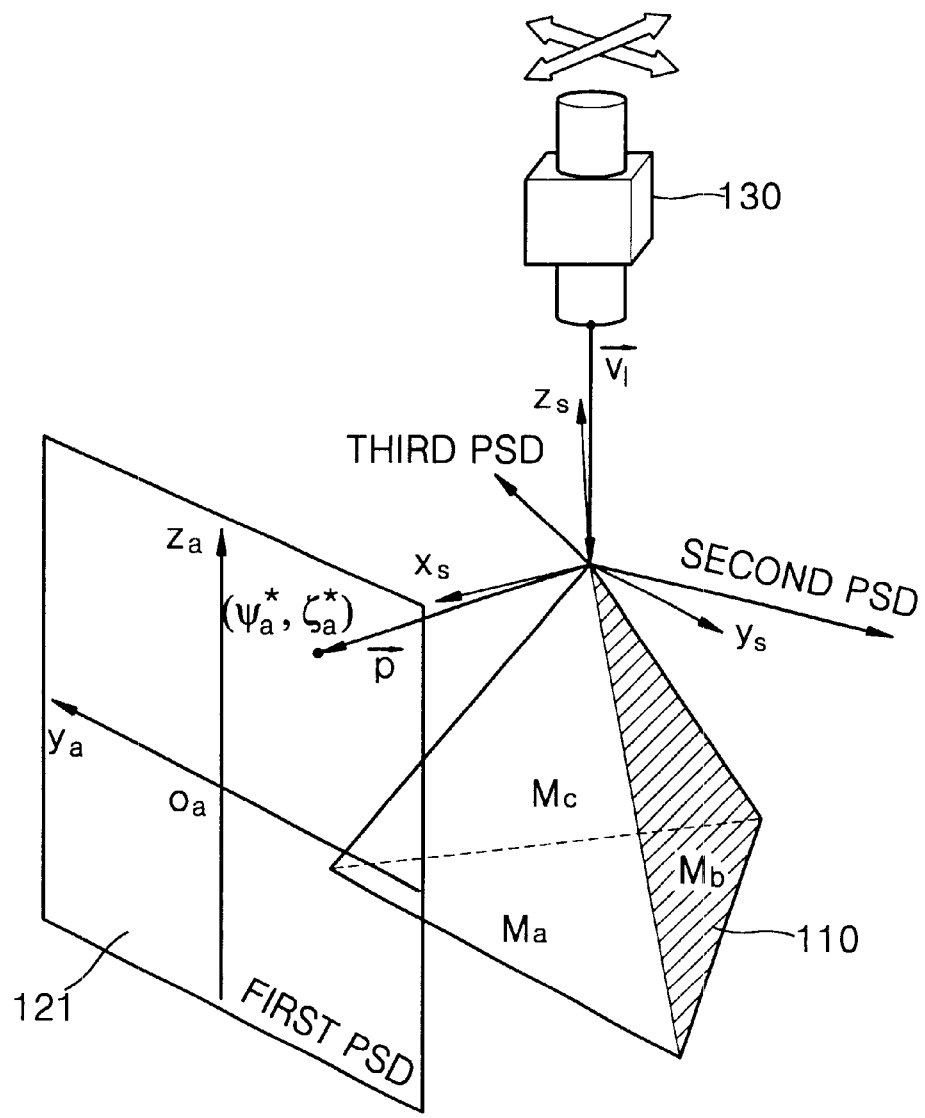
FIG. 7 illustrates an optical phenomenon in the 6-DOF motion measuring apparatus of FIG. 6 under the assumption that the incident laser beam is ideally straight.

FIG. 7 illustrates the incidence of a sub-laser beam reflected from the 3-facet reflector 100 on a PSD with a coordinate system, under the assumption that the laser beam emitted from the laser source 140 is ideally straight. Hereinafter, the three PSDs 121, 122, and 123 will be referred to as the first, second, and third PSDs 121, 122, and 123, respectively. The mirror facets of the 3-facet reflector 110 facing the first, second, and third PSDs 121, 122, and 123 are designated by $M_a$, $M_b$, and $M_c$, respectively. In FIG. 7, parameters for computing the path of a sub-laser beam entering the first PSD 121 after having been reflected from the mirror facet $M_a$ are shown. Here, if the position and orientation the 3-facet reflector 110 with respect to a standard coordinate system are given, a unit vector normal to the surface of the mirror facet $M_a$ of the 3-facet reflector 110 can be calculated through simple analytical geometry. If the unit vector normal to the surface of the mirror facet $M_a$ is $[l_a\ m_a\ n_a]^T$, the reflection matrix of the mirror facet $M_a$ is expressed as:

$$M_a^w = \begin{bmatrix} 1-l_a^2 & -2l_a m_a & -2l_a n_a \\ -2l_a m_a & 1-2m_a^2 & -2n_a m_a \\ -2l_a n_a & -2n_a m_a & 1-2m_a^2 \end{bmatrix} \quad (2)$$

If the direction vector of the laser beam incident on the apex of the 3-facet reflector 100 is $\vec{v}_I^w$, the direction vector of laser beam reflected by the mirror facet $M_a$ is expressed as:

$$\vec{v}_a^w = [v_{ax} v_{ay} v_{az}]^T = M_a^w \vec{v}_I^w \quad (3)$$

Here, the direction vector $\vec{v}_a^w$ of the reflected beam is expressed in the coordinate system $O_w$. The direction vector $\vec{v}_a^w$ is expressed as follows in the coordinate system $O_a$ of the first PSD 121:

$$\vec{p} = [p_x p_y p_z]^T = R_a^{w-1} \vec{v}_a^w \quad (4)$$

where $R_a^{w-1}$ is the inverse matrix of matrix $R_a^w$ which defines a rotation transformation between the coordinate systems $O_w$ and $O_a$.

Figure 8:
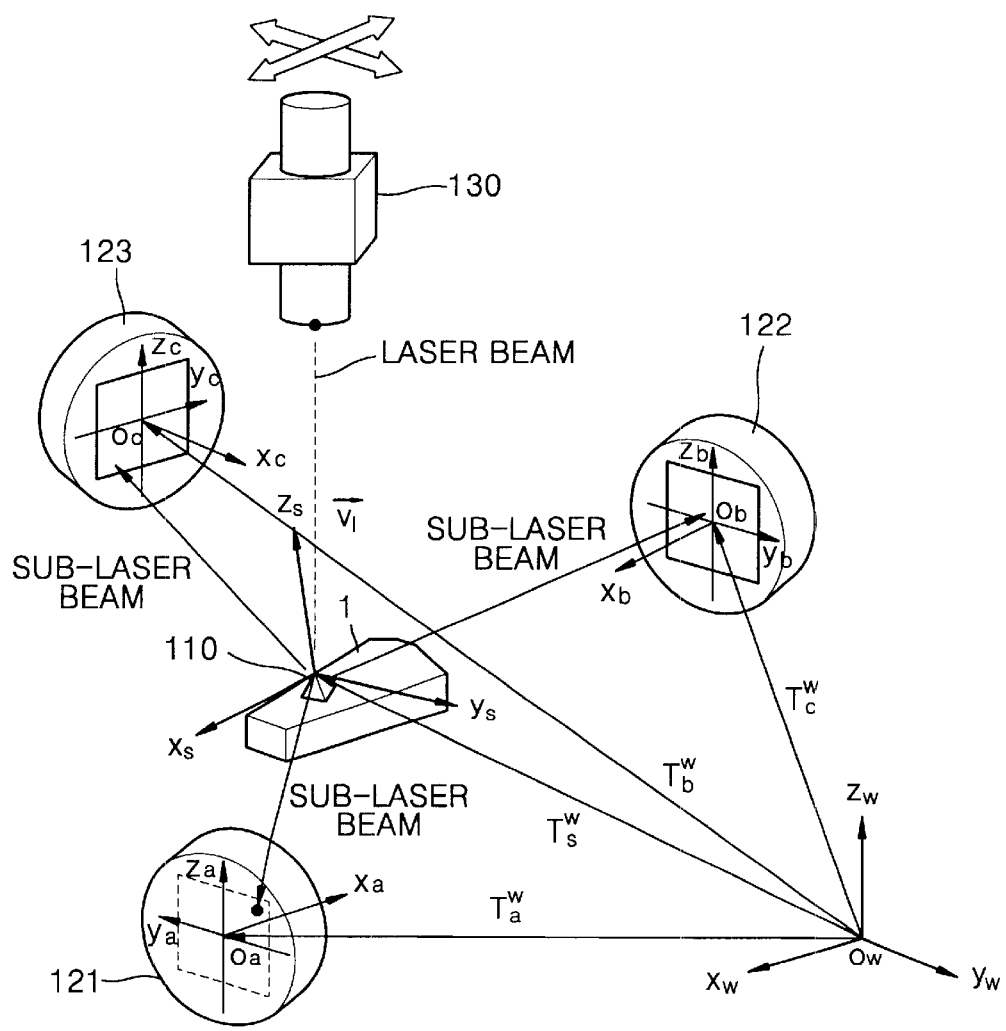
FIG. 8 illustrates the relative positions and orientations of the elements of the 6-DOF measuring apparatus of FIG. 6 using mathematical symbols for analysis.

The position vector $\vec{t}^w$ of the 3-facet reflector 110 is expressed as $\vec{t}^a$ in the coordinate system $O_a$ of the first PSD 121, which can be calculated by:

$$\vec{t}^a = [t_x^a t_y^a t_z^a 1]^T = T_w^a \vec{t}^w \quad (5)$$

where $T_w^a$ is the inverse transform of $T_a^w$ shown in FIG. 8, and $\vec{t}^{1\ w}$ is expressed as:

$$\vec{t}^w = [t_x t_y t_z 1]^T \quad (6)$$

After computing $\vec{p} = [p_x\ p_y\ p_z]^T$ and $\vec{t}^a = [t_x^a\ t_y^a\ t_z^a 1]^T$ through the above procedures, the coordinates $(\psi_a^*, \zeta_a^*)$ of a laser beam spot formed on the first PSD 121 is computed as:

$$\psi_a^* = -\frac{p_y}{p_x} t_x^A + t_y^a$$

$$\zeta_a^* = -\frac{p_z}{p_x} t_x^a + t_z^a. \quad (7)$$

The coordinates of laser beam spots formed on the second PSD 122 and the third PSD 123 are computed in the same manner as for the coordinates of the laser beam spot formed on the first PSD 121 described above. The coordinates of the laser beam spots formed on the surfaces of the second and third PSDs 122 and 123 are expressed as $(\psi_b^*, \zeta_b^*)$ and $(\psi_c^*, \zeta_c^*)$. The coordinates $(\psi_a^*, \zeta_a^*), (\psi_b^*, \zeta_b^*)$ and $(\psi_c^*, \zeta_c^*)$ of the three laser beam spots formed on the first, second and third PSDs 121, 122, and 123 are calculated to be to determine $t_x$, $t_y$, $t_z$, $\gamma$, $\beta$, and $\alpha$ for 6-DOF displacement.

Figure 9:
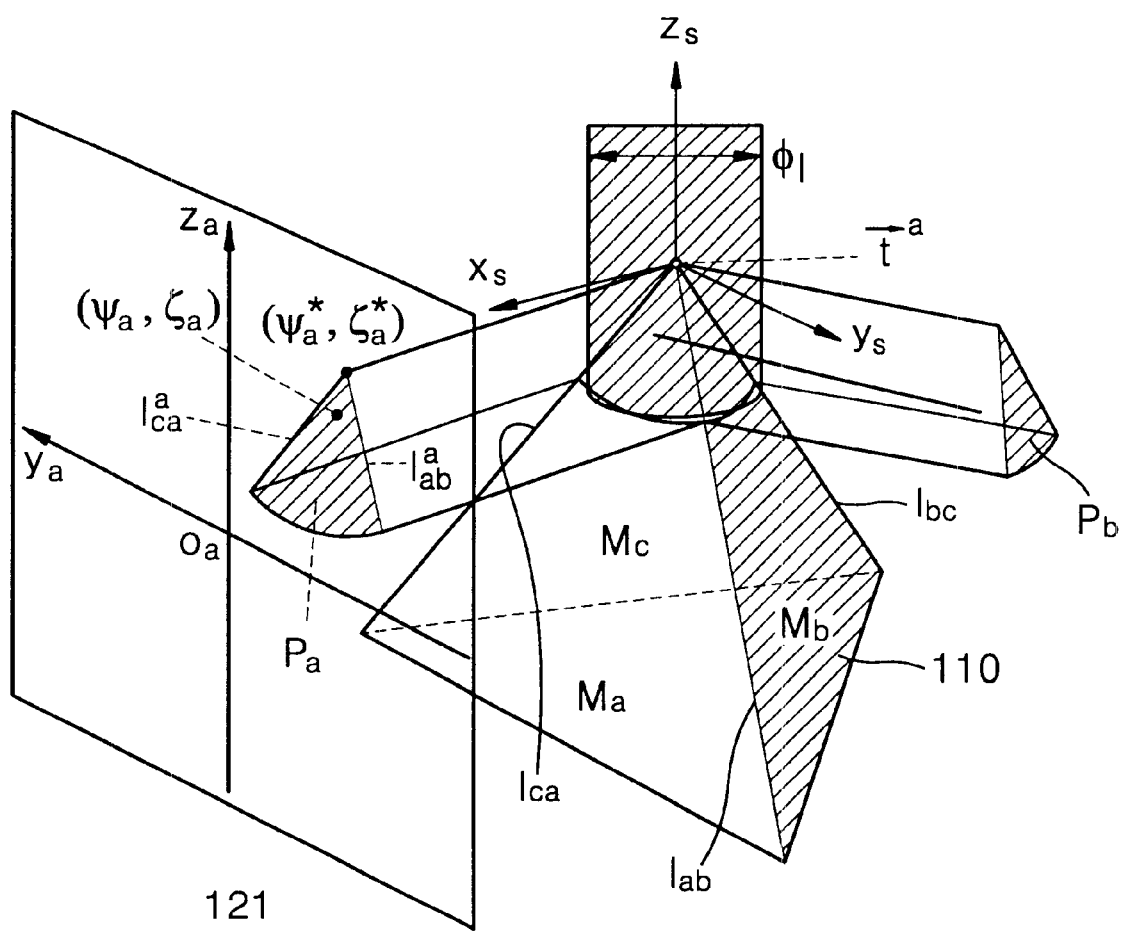
FIG. 9 illustrates an optical phenomenon in the 6-DOF measuring apparatus of FIG. 6 in which the intensity profile of the incident laser beam is assumed to be Gaussian.

A simulation test performed using a laser beam under the assumption that the laser beam has a Gaussian intensity profile will be described. FIG. 9 illustrates the detection by the first PSD 121 of a laser beam having a diameter $\Phi_I$ reflected by the 3-facet reflector 110, which is almost the same as a real situation. The coordinates $(\psi_a^*, \zeta_a^*), (\psi_b^*, \zeta_b^*)$ and $(\psi_c^*, \zeta_c^*)$ output from the first, second, and third PSDs 121, 122, and 123, which are derived above, are based on the assumption that the incident laser beam is infinitely narrow. However, actual laser beam is a circular light beam having an arbitrary diameter.

As shown in FIG. 9, a laser beam is incident on the apex of the 3-facet reflector 110 and is split into three sub-laser beams by the three mirrors of the 3-facet reflector 110. Each of the split and reflected sub-laser beams has a fan-shaped cross-section, as shown in FIG. 9. This is because the three face mirrors of the 3-facet reflector 110 are triangular. As the fan-shaped sub-light beams are incident on the first, second, and third PSDs 121, 122, and 123, the first, second, and third PSDs 121, 122, and 123 output the intensity at the center of intensity of the fan-shaped sub-light beams as electric signals. In FIG. 9, the location of the center of intensity of the laser beam spot formed on the surface of the first PSD 121 is expressed as $(\psi_a, \zeta_a)$.

The coordinates $(\psi_a, \zeta_a)$ are the center of the intensity distribution of the laser beam over the fan-shaped cross-section and are slightly below the coordinate $(\psi_a^*, \zeta_a^*)$ of the laser beam formed on the first PSD 121 which is calculated under the assumption that laser beam is infinitely narrow.

Hereinafter, a process of calculating the outputs of the first, second, and third PSDs 121, 122, and 123 in consideration of the laser intensity distribution will be described.

According to the present invention, it is assumed that the laser beam before reflection is a Gaussian beam having a circular cross-section. If the intensity of the laser beam is P and the diameter of the laser beam is $\Phi_I$, the intensity of the laser beam has a Gaussian distribution expressed as, $$I(r) = \frac{8P}{\pi \phi_l^2} \exp\left(-\frac{8r^2}{\phi_l^2}\right) \quad (8)$$

where r is the radial distance from the center axis of laser beam to any point of interest, and I(r) is the intensity of the laser beam per unit area.

Figure 10:
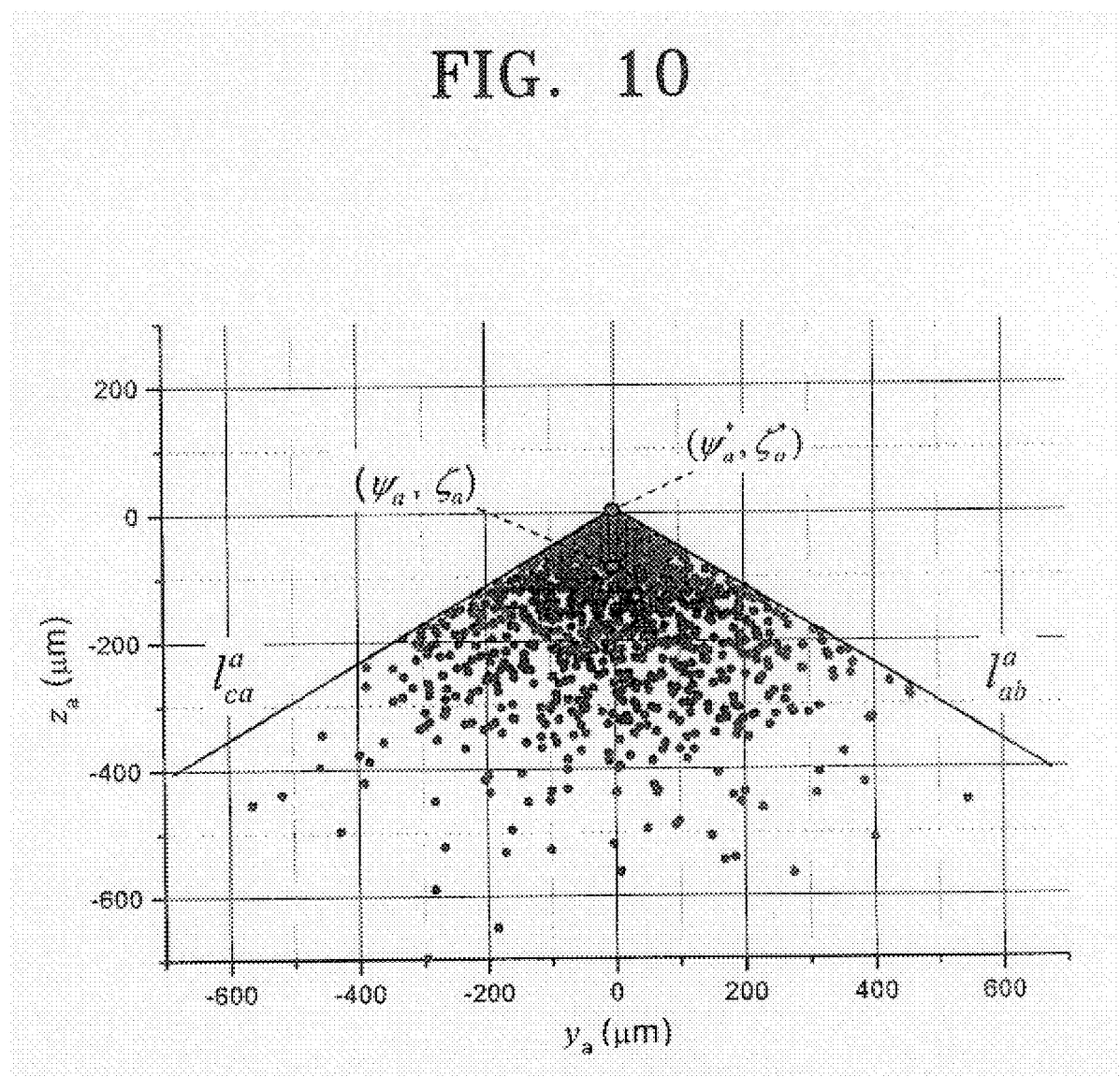
FIG. 10 illustrates the intensity distribution of laser beam spots formed on the first position-sensitive detector (PSD) of FIG. 9.

The laser beam having the above intensity distribution is split into three sub-laser beams by the 3-facet reflector 110, and one of the three sub-laser beams is intercepted by and forms a fan-shaped spot on the surface of the first PSD 121. Referring to FIG. 10, spots are used to show the intensity distribution within the fan-shaped spot. Here, the density of the spots is proportional to the intensity of the laser beam. The intensity of laser beam varies according to the angle of incident of the laser beams on the first, second, and third PSDs 121, 122, and 123, and the diameter $\Phi_I$ of the laser beam emitted from the laser source 130. FIG. 10 illustrates a case where a laser beam reflected from the 3-facet reflector 110 is incident on the first PSD 121 at a 90° angle and the laser beam has a diameter $\Phi_I$ of 460 μm. If the fan-shaped cross-section of the laser beam spot formed on the first PSD 121 is $P_a$, $l_{ab}^a$ and $l_{ca}^a$ represent the two sides of the fan-shaped plane $P_a$. The two sides $l_{ab}^a$ and $l_{ca}^a$ formed on the first PSD 121 are the projections of the sides $l_{ab}$ and $l_{ca}$ of the 3-facet reflector 110. The center of intensity $(\psi_a, \zeta_a)$ of the sub-laser beam spot $P_a$ formed on the first PSD 121, assuming that the laser beam before reflection has a Gaussian intensity distribution, is calculated by integration as follows:

$$\psi_a = \frac{\int_{P_a} \int y_a I_a(r_a) dy_a dz_a}{\int_{P_a} \int I_a(r_a) dy_a dz_a} \quad (9)$$

$$\zeta_a = \frac{\int_{P_a} \int z_a I_a(r_a) dy_a dz_a}{\int_{P_a} \int I_a(r_a) dy_a dz_a}$$

where $r_a$ and $l_a(r_a)$ are expressed by $$r_a = \sqrt{(y_a - \psi_a^*)^2 \frac{p_x^2}{p_x^2 + p_y^2} + (z_a - \zeta_a^*) \frac{p_x^2}{p_x^2 + p_x^2}} \quad (10)$$

$$I_a(r_a) = \frac{\vec{p} \cdot x_a}{\|\vec{p}\|} I(r_a).$$

The centers of intensity $(\psi_b, \zeta_b)$ and $(\psi_c, \zeta_c)$ of the sub-laser beam spots $P_b$ and $P_c$ formed on the second and third PSDs 122 and 123, assuming that the laser beam before reflection has a Gaussian intensity distribution, are calculated by the same procedures. The outputs $(\psi_a, \zeta_a)$, $(\psi_b, \zeta_b)$, and $(\psi_c, \zeta_c)$ of the three PSDs 121, 122, and 123 are used in measuring the 6-DOF displacement of the 3-facet reflector 110 by calculating as $t_x$, $t_y$, $t_z$, $\gamma$, $\beta$, and $\alpha$.

6-DOF displacement measurement by a numerical method will be described in greater detail. The procedures of calculating the outputs $(\psi_a, \zeta_a)$, $(\psi_b, \zeta_b)$, and $(\psi_c, \zeta_c)$ of the three PSDs 121, 122, and 123 to be used in computing $t_x$, $t_y$, $t_z$, $\gamma$, $\beta$, and $\alpha$ for 6-DOF displacement of the 3-facet reflector 110 are described. However, in actual measurement, 6-DOF displacement of the 3-facet reflector 110 is measured with given $(\psi_a, \zeta_a)$, $(\psi_b, \zeta_b)$, and $(\psi_c, \zeta_c)$. This is performed using Newton's method, which approximates the solution to a multi-variable equation, in the present invention.

Figure 11:
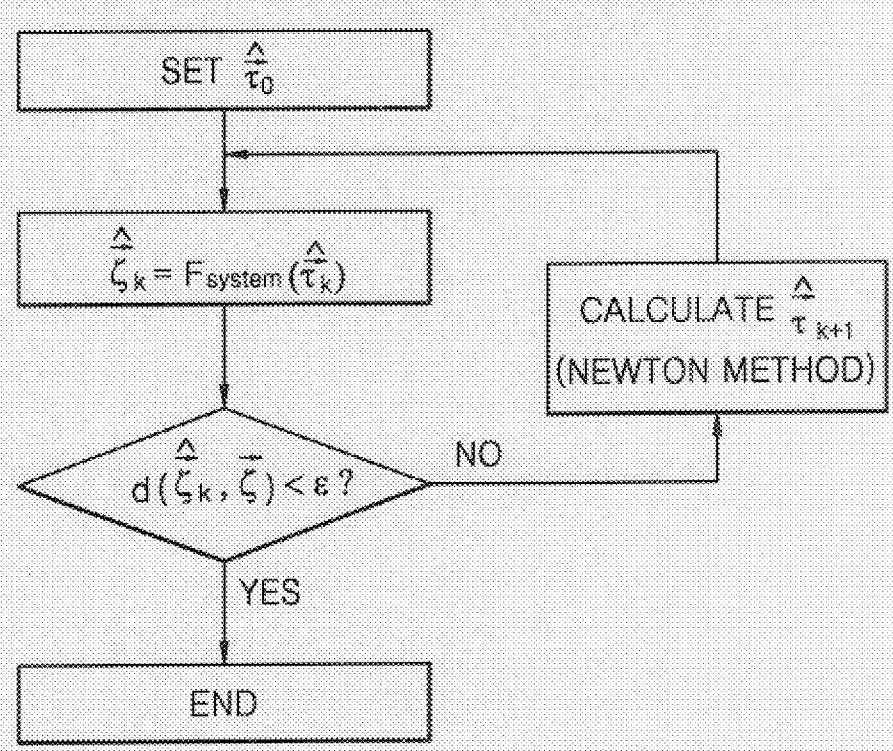
FIG. 11 is a flowchart illustrating a numerical analysis method applied to measure the 6-DOF motion of the 3-facet reflector using the output values from the PSDs according to the present invention.

FIG. 11 is a flowchart illustrating the numerical analysis method applied to measure the 6-DOF of the 3-facet reflector using the outputs from the PSDs. As shown in FIG. 11, if the 6-DOF displacement of the 3-facet reflector 110 is expressed as the vector $\vec{\tau} = [t_x \; t_y \; t_z \; \gamma \; \beta \; \alpha]^T$ and the outputs from the first, second, and third PSDs 121, 122, and 123 are expressed as the 1-dimensional vector; $\vec{\zeta} = [\psi_a \; \zeta_a \; \psi_b \; \zeta_b \; \psi_c \; \zeta_c]^T$, a predetermined vector function $F_{system}$ exists such that:

$$\vec{\zeta} = F_{system}(\vec{\tau}) \quad (11)$$

As expressed by relation (11), if a 6-DOF displacement $\vec{\tau}$ of the 3-facet reflector 110 is given, the outputs of the three PSDs 121, 122, and 123 can be calculated with the function $F_{system}$. In other words, using the inverse of $F_{system}$, the 6-DOF displacement of the 3-facet reflector 110 can be measured. If the 1-dimensional vector $\vec{\zeta}$ for the outputs from the first, second, and third PSDs 121, 122, and 123 is given in an actual measurement, an estimate $$\hat{\vec{\tau}}$$

which is close to $\vec{\tau}$ is calculated to obtain $\vec{\tau}$ which satisfies relation (11). First, the initial estimate $$\hat{\vec{\tau}}_0$$

is set. Subsequently, as shown in FIG. 11, calculation and new estimation are iterated. Once the estimate $$\hat{\vec{\zeta}}_k$$

for the output vector $\vec{\zeta}$ of the PSDs 121, 122, and 123 is calculated for an arbitrary estimate $$\hat{\vec{\tau}}_k,$$

the calculated estimate $$\hat{\vec{\zeta}}_k$$

is compared with the original output vector $\vec{\zeta}$ of the PSDs 121, 122, and 123. For this comparison, a predetermined value $\epsilon$ is used to define an acceptable error range (tolerance). In particular, if the difference between the two vectors is $$d(\hat{\vec{\zeta}}_k, \vec{\zeta}),$$

and the difference $$d(\hat{\vec{\zeta}}_k, \vec{\zeta})$$

is within the predetermined tolerance $\epsilon$, iteration stops. After the evaluation for the estimate output vector $$\hat{\vec{\zeta}}_{k+1}$$

of the PSDs 121, 122, and 123, a next estimate $$\hat{\vec{\zeta}}_k$$

is calculated by Newton's method.

The structure in which the laser light source tracks the 3-facet reflector will be described in greater detail. To measure the 6-DOF displacement of the object 1 according to the principle described above, a laser light beam should be incident on the apex of the 3-facet reflector 110 mounted on the object 1. The center of the laser beam must be aligned with the apex of the 3-facet reflector 110 to obtain accurate measurement results. This is achieved in the present invention by synchronizing the motion of the laser beam along with the movement of the 3-facet reflector 100. As shown in FIG. 6, the laser source 130 can move in a 2 dimensional plane. If the center of the laser beam incident on the 3-facet reflector 110 is not aligned with the apex of the 3-facet reflector 110, the intensities of the three sub-laser beams reflected from the 3-facet reflector 110 are different. Meanwhile, if the center of the incident beam is aligned with the apex of the 3-facet reflector 110, the three reflected sub-laser beams have the same intensity. Each of the first, second, and third PSDs 121, 122, and 123 can measure the intensities of sub-laser beams as well as their locations. In the present invention, the center of the incident laser beam can be accurately aligned with the apex of the 3-facet reflector 100 by comparing the intensities of the sub-laser beams incident on the three PSDs 121, 122, and 123. Although the 3-facet reflector 110 moves, the laser beam emitted from the laser source 130 can accurately track the apex of the 3-facet reflector 110 by continuously comparing the intensities of sub-laser beams incident on the three PSDs 121, 122, and 123 in the above-described way. A method of controlling this tracking system is illustrated in FIG. 6. If the 3-facet reflector 110 moves fast, an automatic tracking system such as a motor is needed. If the 3-facet reflector 110 moves slowly, tracking of the apex of the 3-facet reflector 110 can be manually controlled for displacement measurement.

The 6-DOF measuring apparatus according to the present invention described above can be applied to an optical system for measuring the motion of a slider during operation of a hard disc drive (HDD), which is a kind of disc type information storage media.

Figure 12:
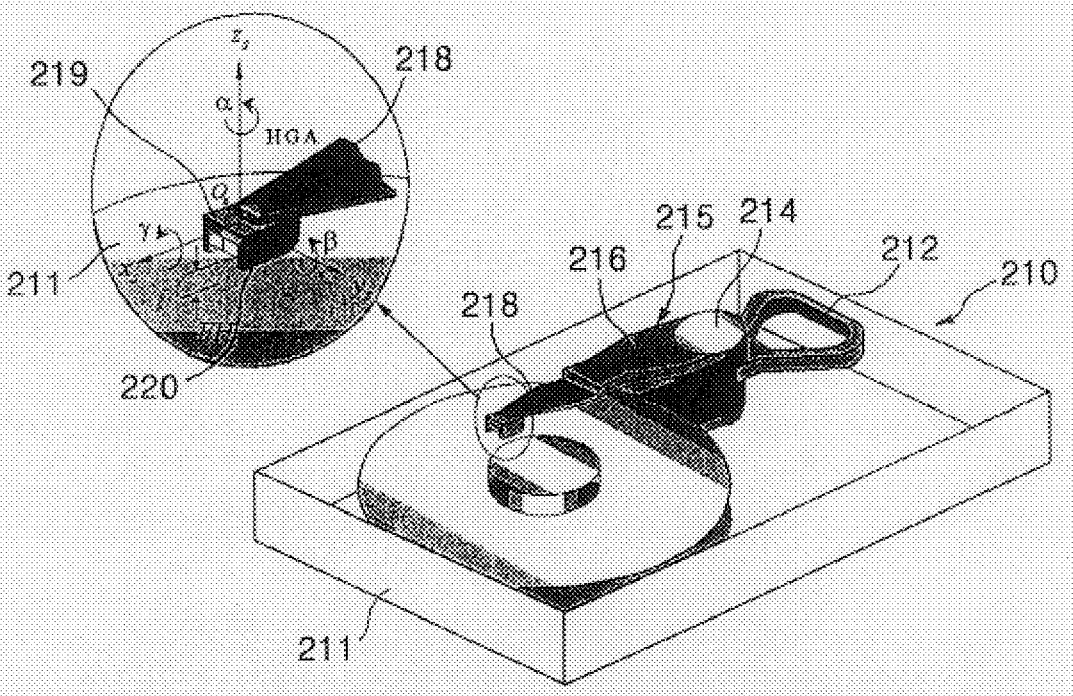
FIG. 12 illustrates the motion of a slider over a magnetic disc in a hard disc drive (HDD)

The motion of a slider in a HDD will be described. FIG. 12 illustrates the motion of a slider over a magnetic disc in a HDD. As shown in FIG. 12, a slider 220 is fixed to the front end of a swing arm 215 and is positioned over a magnetic disc 211 of a HDD 210. A voice coil motor (VCM) 212 as an actuator for driving the slider 220 is mounted at the rear end of the swing arm 215. The swing arm 215 includes an E-block 216 as a rigid body, a suspension 218 as an elastic body, and a flexure 219. The E-block 216 is connected to the top of a pivot 214 and extends in the direction of the magnetic disc 211, and the suspension 218 is connected to the front end of the E-block 216. The flexure 219 is connected to the front end of the suspension 218, and the slider 220 is fixed to the bottom of the flexure 219. As the magnetic disc 211 turns on the HDD 210 having this configuration, the slider 200 hovers on air a predetermined distance above the magnetic disc 211 by an air bearing effect acting between the magnetic disc 211 and the slider 220. The position of the slider 220 is maintained by the VCM 212. In a normal operation state where the speed of rotation of the magnetic disc 211 is constant, the distance, i.e., the flying height (FH) of the slider 220 above the magnetic disc 211 is kept constant.

On the other hand, when data recording or reproduction is performed in the HDD 210, the slider 220 tracks along a particular track or moves from a track to another track. In the tracking mode, the flying height (FH) of the slider 220 above the magnetic disc 211 is kept constant, and the orientation of the slider 220 is also constant. Meanwhile, in the track searching mode where the slider 220 moves from a track to another track, the swing arm 215 pivots about the pivot 214, so that the slider 220 moves along a circular arc trajectory. In the track searching mode, the speed of movement of the slider 220 suddenly increases or decreases by the actuator. As a result, the suspension 218 and the flexure 219 deform, thereby changing the orientation of the slider 220.

To increase the data recording density of the HDD 210, it is preferable to minimize the flying height (FH) of the slider 220 above the magnetic disc 211. To increase the speed of operation of the HDD, the swing arm 215 must be operated at high speed such that the slider 220 moves fast over the magnetic disc 211. However, as the flying height (FH) of the slider 220 above the magnetic disc 211 becomes small, it is likely that the slider 220 strikes the magnetic disc 221. The higher the driving speed of the slider, the higher the likelihood of the slider striking the magnetic disc 221. In the research and development of high-speed and high-capacity HDDs, many trials and errors have been made to overcome this problem. To maintain the flying height (FH) of the slider 220 above the magnetic disc 221, there is a need for quantitative examination of the dynamic characteristics of the slider, which are influenced by the actuator, swing arm, and air bearing effects, so that the HDD can be designed based on the results of the quantitative examination.

Figure 13:
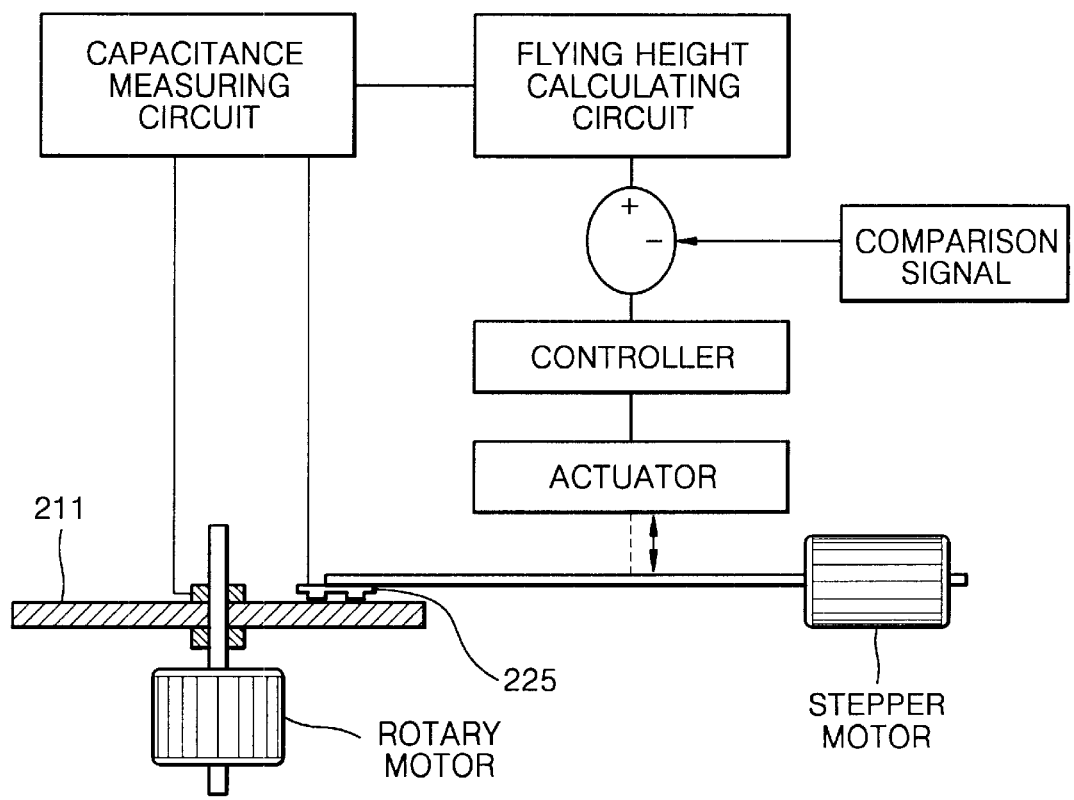
FIG. 13 is a schematic view of a conventional system for measuring the flying height (FH) of a HDD slider.

Much research on the quantitative measurement of the dynamic characteristics of a slider has been published. FIG. 13 is a schematic view of a conventional system for measuring the flying height (FH) of a HDD slider. As shown in FIG. 13, the conventional system for measuring the flying height (FH) of the slider 255 above the magnetic disc 211 measures the flying height (FH) with a capacitance sensor, wherein the magnetic disc 211 has a predetermined pattern formed of a conducting material at its surface, and the slider 255 has rails formed of a conducting material.

Figure 14:
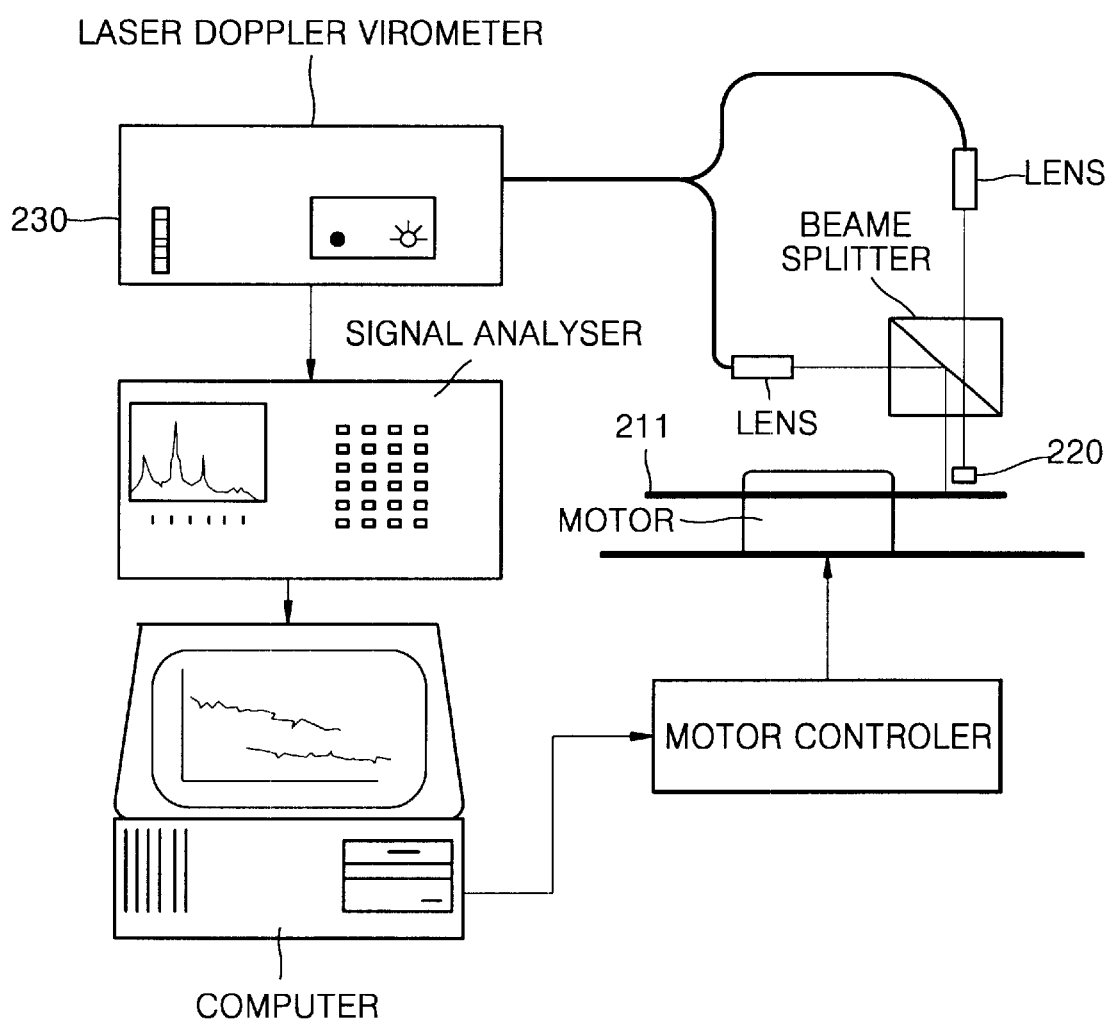
FIG. 14 is a schematic view of a conventional system for measuring the flying height (FH), rolling angle, and pitching angle of a HDD slider.

FIG. 14 is a schematic view of a conventional system for measuring the flying height (FH), rolling angle, and pitching angle of a HDD slider. As shown in FIG. 14, the conventional measuring system measures the flying height (FH) of the slider 220 above the magnetic disc 211, and the rolling and pitching angles using two laser beams emitted from a laser doppler vibrometer.

Figure 15:
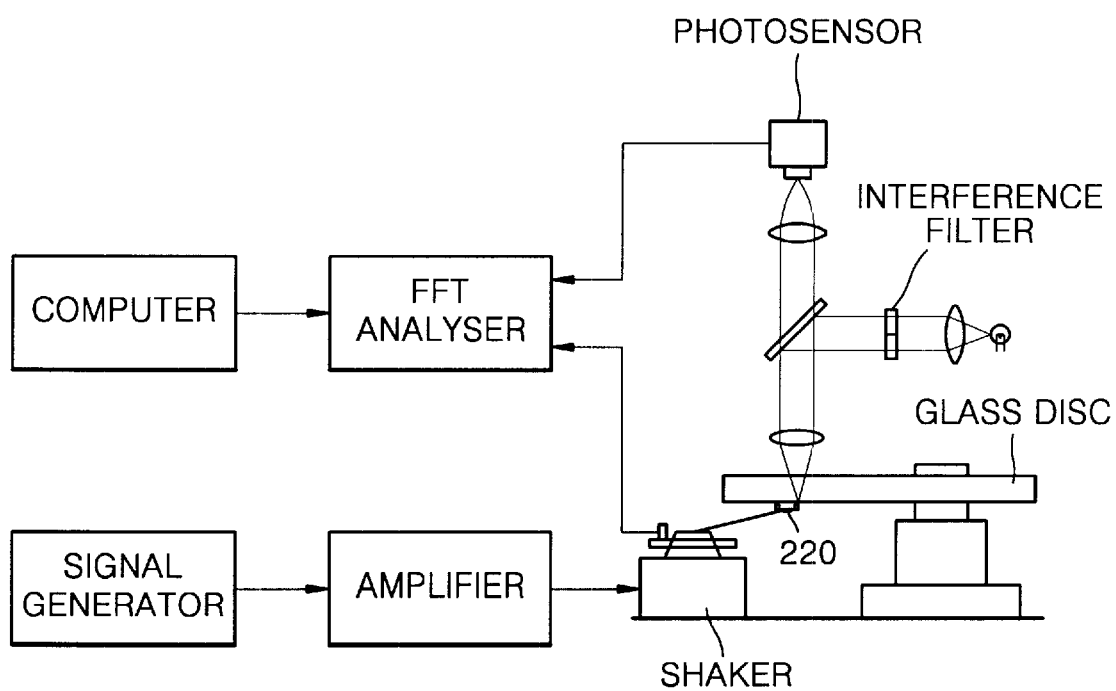
FIG. 15 is a schematic view of a conventional system for measuring the flying height (FH) of a HDD slider using a photosensor.

FIG. 15 is a schematic view of a conventional system for measuring the flying height (FH) of a HDD slider using a photosensor. The conventional system of FIG. 15 measures the flying height (FH) of the slider 220 above the magnetic disc using laser interference. As shown in FIG. 15, the flying height (FH) can be measured through the rear surface of the disc by using a transparent glass disc instead of a magnetic disc.

The previously mentioned conventional systems for measuring the motion of a HDD slider are implemented to measure tracking of the slider, so that they are limited to measuring the flying height (FH) of the slider above the magnetic disc, and the rolling and pitching angles. In other words, the conventional measuring systems are not associated with the measurement of rapid displacement of the slider, which occurs when the slider searches for tracks. This drawback of the conventional techniques can be solved using the 6-DOF motion measuring apparatus according to the present invention. In particular, the present invention also provides a structurally simple swing arm type optical system capable of accurately measuring dynamic characteristics of a HDD slider according to tracking and searching motion, and capable of measuring 6-DOF motion of the HDD slider.

Prior to describing preferred embodiments of the swing arm type optical system capable of measuring the 6-DOF motion of a HDD slider according to the present invention, a 6-DOF motion measuring apparatus using a 3-facet reflector will be described below.

Figure 16:
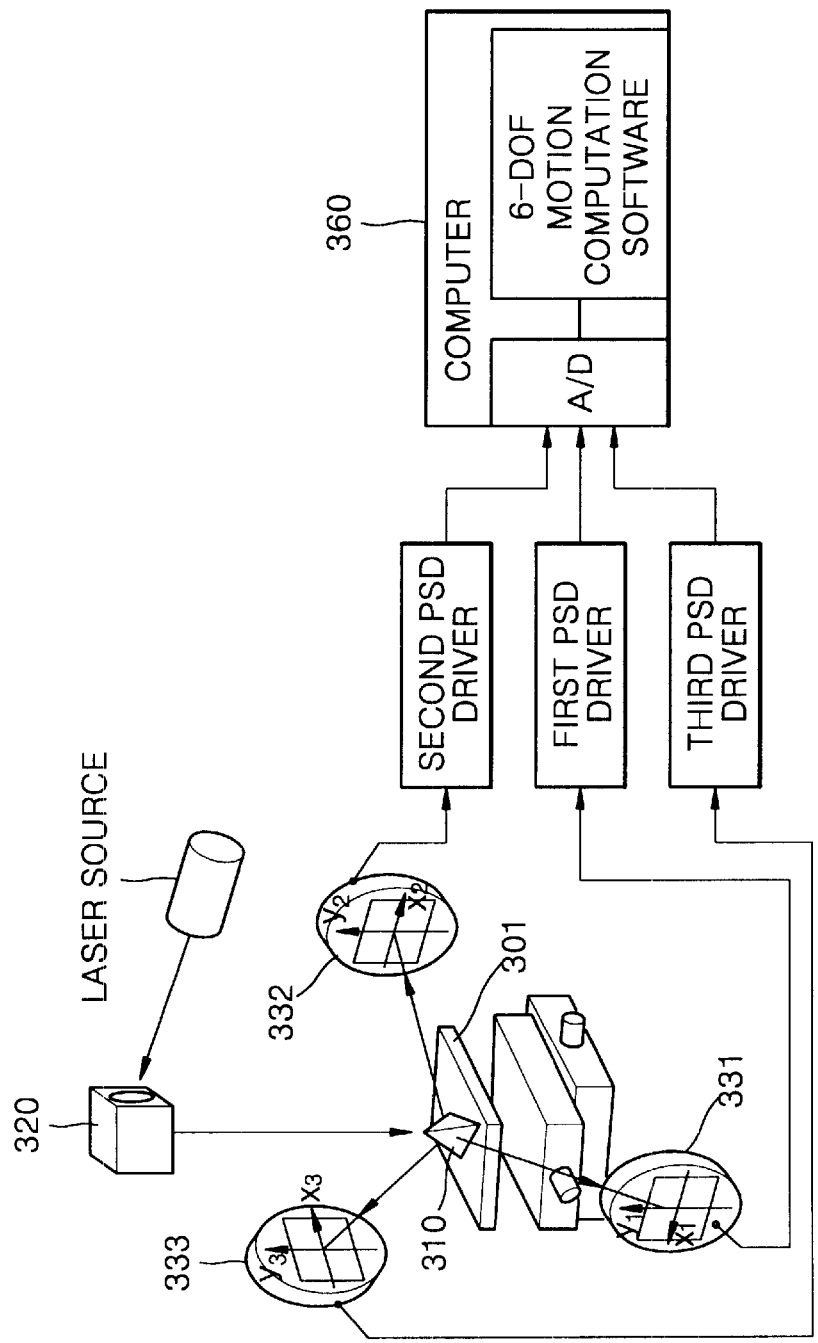
FIG. 16 is a view of a system for measuring the 6-DOF motion of an object using a 3-facet reflector.
Figure 17:
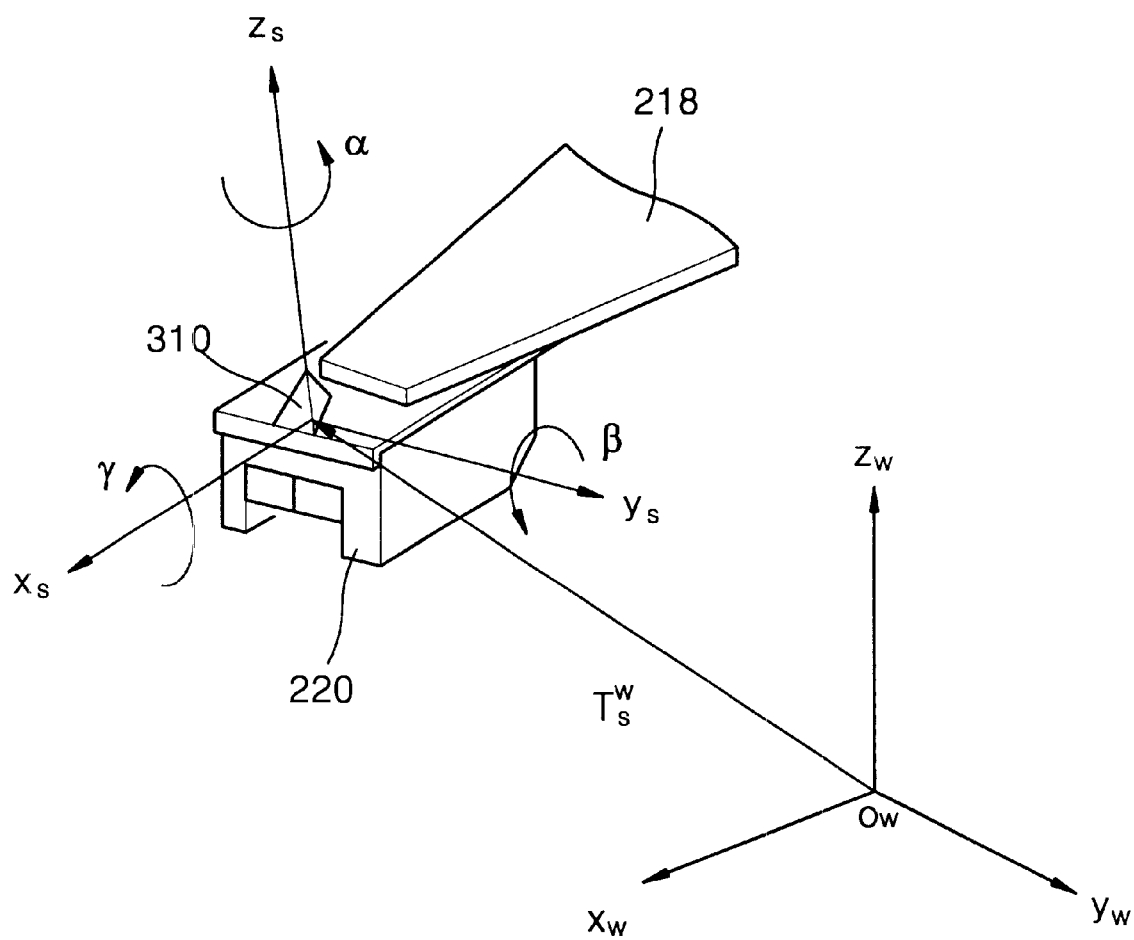
FIG. 17 is a schematic view illustrating the 6-DOF motion of a slider of a swing arm type optical system using coordinates systems.
Figure 18:
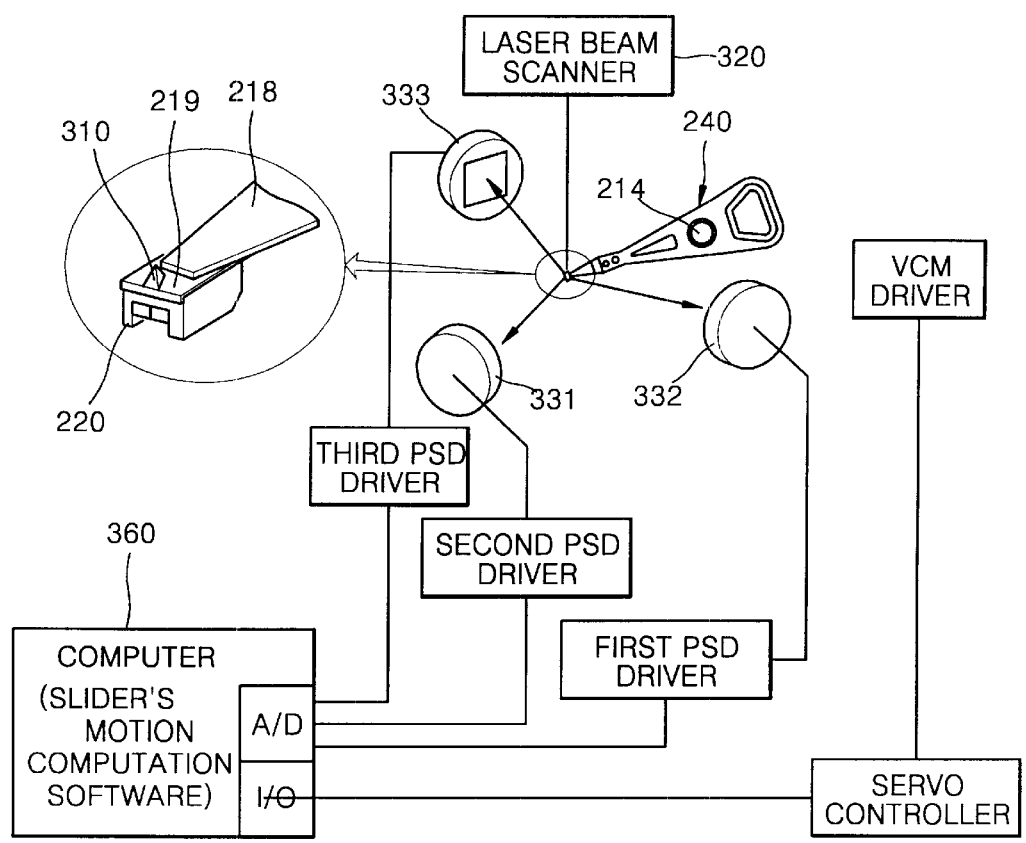
FIG. 18 is a view of a swing arm type optical system to which the 6-DOF measuring system of FIG. 16 is applied to measure the 6-DOF motion of the slider.

FIG. 16 is a view of a system for measuring the 6-DOF motion of an object using a 3-facet reflector. FIG. 17 is a schematic view illustrating the 6-DOF motion of a slider of a swing arm type optical system using coordinates systems. FIG. 18 is a view of a swing arm type optical system to which the 6-DOF motion measuring system of FIG. 16 is applied to measure the 6-DOF motion of the slider.

Referring to FIG. 16, a 3-facet reflector 310 is fixed to the top of an object 301 whose 6-DOF motion is to be measured. As described previously, the 3-facet reflector 310 is an embodiment of the multidirectional reflector having at least 3 reflecting sides according to the present invention. According to the present invention, the multidirectional reflector having at least three reflecting sides is used so that the incident laser beam is split into at least three sub-laser beams and three of the three or more beams reflected from the multidirectional reflector in different directions are used to measure 6-DOF motion.

The multidirectional reflector or the 3-facet reflector 310 may be manufactured as a separate unit and then mounted on the object 301, or a slider 220 or flexure 218 to be described below. Alternatively, the multidirectional reflector or the 3-facet reflector 310 may be formed as a single unit along with the object 301, the slider 220, or the flexure 218 as needed. The relative positions of the slider and the multidirectional reflector or 3-facet reflector are fixed. The structure or installation of the multidirectional reflector or 3-facet reflector can be varied without limitation.

As a laser beam is incident on the apex of the multidirectional reflector or 3-facet reflector 310 at which the three reflecting sides meet, it is split into three sub-laser beams which are then reflected at an angle of 120 degrees. The three reflected sub-laser beams are received by three PSDs 331, 332, and 333, and the parameters $t_x$, $t_y$, $t_z$, rolling angle, pitching angle, and yawing angle for the 6-DOF motion of the 3-facet reflector 310 mounted on the object 301 are calculated using the above-described mathematical procedure according to the present invention. The 6-DOF motion of the 3-facet reflector 301 is measured as the 6-DOF motion of the object 301.

As shown in FIG. 17, the motion of a slider in a swing arm type optical system can be expressed using coordinate systems. The major motion of the slider 220 includes rotation (rolling) of the slider 220 about the Xs axis (parallel to the longitudinal direction of the flexure 218 connected to the swing arm (see FIG. 18)), rotation about the Ys axis (parallel to the lateral direction of the flexure 218), and height variation along the Zs axis (up and down motion).

Referring to FIG. 18, when the slider 220 searches for a track, the slider 220 pivots about the pivot 214 of the swing arm 240 along a circular arc trajectory. A laser beam scanner 320 must track the motion of the slider 220 mounted at the front end of the suspension 218, so that a laser beam emitted from the laser beam scanner 320 is incident precisely on the apex of the 3-facet reflector 310 mounted on the slider 220. If the object, i.e., the slider 220 moves slowly, a galvanometer scanner or a precision transfer apparatus can be used such that the laser beam is accurately incident on the apex of the 3-facet reflector. However, if the HDD slider moves fast, it is difficult to kept the laser beam incident precisely on the apex of the 3-facet reflector.

Figure 19:
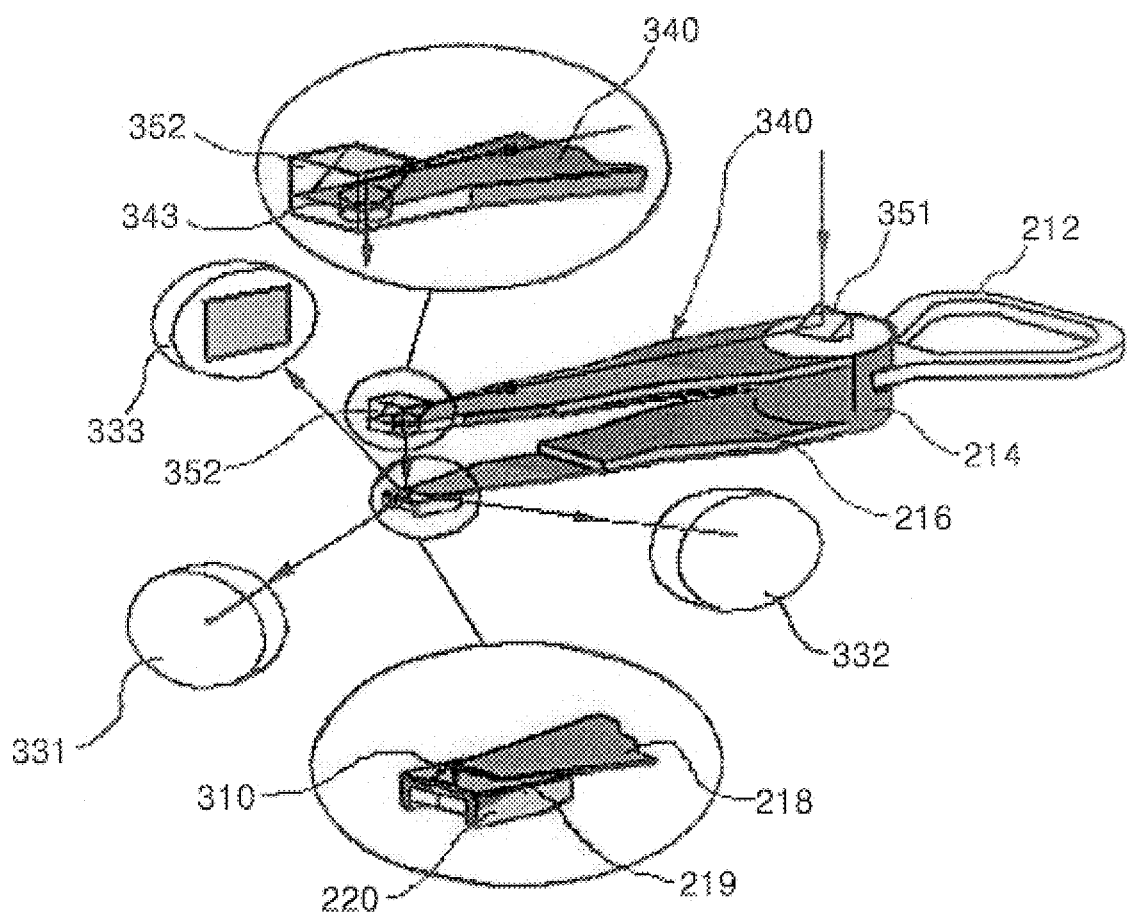
FIG. 19 is a view of a preferred embodiment of a swing arm type optical system according to the present invention capable of measuring the 6-DOF motion of a HDD slider.
Figure 20:
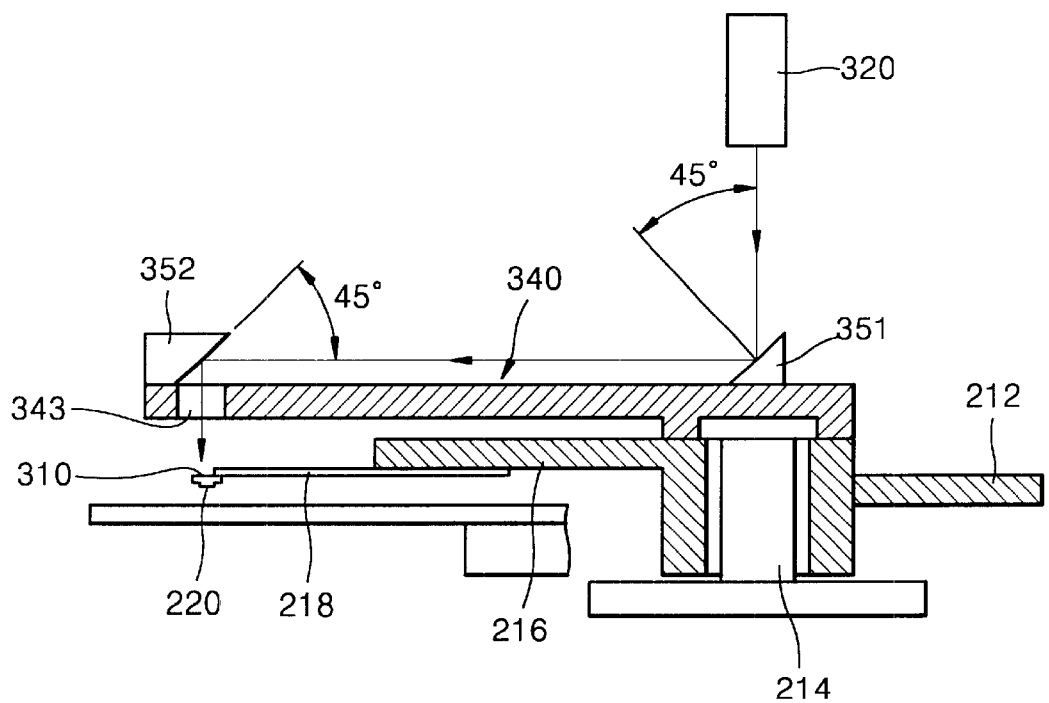
FIG. 20 is a sectional view of the swing arm type optical pickup of FIG. 19.
Figure 21:
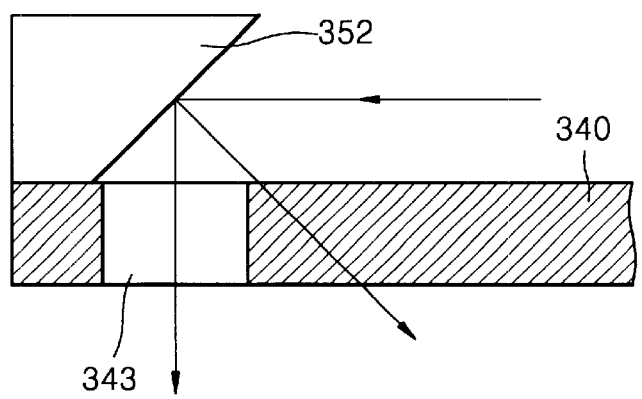
FIG. 21 is a view of a second reflector mounted at the front end of the 2-stage swing arm of FIG. 19.
Figure 22:
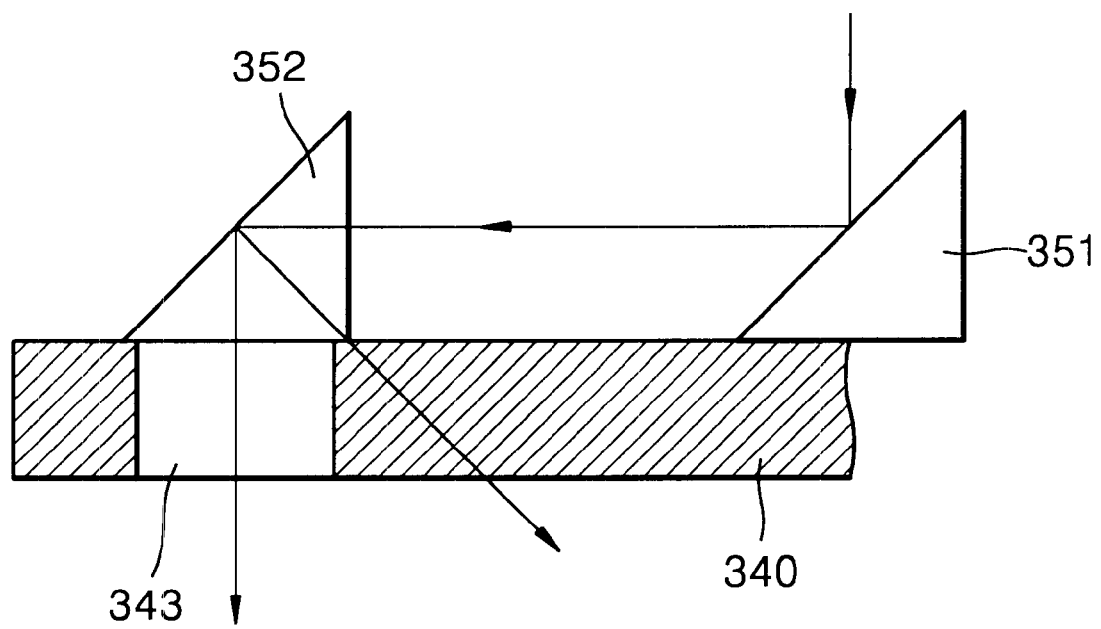
FIG. 22 shows another embodiment of the second reflector of the swing arm type optical system of FIG. 19.

FIG. 19 is a view of a preferred embodiment of a swing arm type optical system according to the present invention capable of measuring the 6-DOF motion of a HDD slider. FIG. 20 is a sectional view of the swing arm type optical pickup of FIG. 19. FIG. 21 is a detailed view of a second reflector mounted at the front end of the 2-stage swing arm of FIG. 19. FIG. 22 shows another embodiment of the second reflector of the swing arm type optical system of FIG. 19.

Referring to FIG. 19, the swing arm 340 of the optical system consists of parallel upper and lower swing arms in two stages, and the rear ends of the upper and lower swing arms are connected by the pivot 204. The 2-stage swing arm 340 pivots about the pivot 214. The lower swing arm includes the E-block 216, the suspension 218, and the flexure 219, which are sequentially connected, and the slider 220 is fixed to the bottom of the flexure 219. The voice coil motor (VCM) 212 as an actuator for driving the slider 220 is installed at the rear end of the 2-stage swing arm 340. The upper swing arm is formed of a rigid body which is does not elastically deformed very much.

The 3-facet reflector 310 is fixed to the top of the slider 220. A through hole 343 is formed at the front end of the upper swing arm aligned with the apex of the 3-facet reflector 310. A first reflector 351 and a second reflector 352 are fixed at the top of the upper swing arm. The first and second reflectors 351 and 352 are hexahedrons each having a 45-degree sloping side. The first reflector 351 is located on the top of the pivot 214 so that its 45-degree sloping side faces the front end of the upper swing arm. The second reflector 352 is located at the front end of the upper swing arm so that its 45-degree sloping side faces the sloping side of the first reflector 351, and a laser beam reflected by the sloping side of the second reflector 352 is incident on the apex of the 3-facet reflector 310 through the through hole 343 formed at the upper swing arm.

Referring to FIGS. 20 and 21, a laser beam emitted from the laser beam scanner 320 is incident on the sloping side of the first reflector 351 located at the top of the pivot 214. The laser beam reflected by the first reflector 351 goes toward the sloping side of the second reflector 352. The laser beam reflected by the second reflector 352 is incident on the apex of the 3-facet mirror 310 through the through hole 343 of the upper swing arm.

The laser beam incident on the apex of the 3-facet reflector 310 is reflected into three sub-laser beams at an angle of 120 degrees. As shown in FIG. 18, three PSDs 331, 332, and 333 are disposed in the traveling paths of the three reflected sub-laser beams. The sub-laser beams received by the PSDs 331, 332, and 333 are input to a controller 360 as electric signals. The controller 360 calculates the centers of intensity of the three sub-laser beam spots using the electric signals assuming that he intensity distribution of the laser beam is Gaussian, as the intensities of the sub-laser beams received by the PSDs 331, 332, and 333, and measures the 6-DOF motion of the 3-facet reflector 310 using the calculated intensities of the sub-laser beams.

According to the present invention, although the 2-stage swing arm 340 on which the slider 200 is mounted moves rapidly along a track and across tracks, the laser beam scanned from the laser beam scanner 320 is incident precisely on the apex of the 3-facet reflector 310 at all times because the first and second reflectors 351 and 352 and the 3-facet reflector 310 also move along with the 2-stage swing arm 340. As a result, the PSDs 331, 332, and 333 can generate voltage signals from the three sub-laser beams reflected from the 3-facet reflector 310 with increased reliability, so that the 6-DOF displacement of the slider 220 can be accurately measured.

The sloping sides of the first and second reflectors 351 and 352 are mirrors coated with metal such as aluminum (Al). Alternatively, as shown in FIG. 22, a transparent prism may be used as the second reflector 352. In this case, the second reflector 352 is fixed to cover the through hole 343 formed at the upper swing arm, as shown in FIG. 22, so that the laser beam reflected from the first reflector 351 is incident into the second reflector 352 and reflected downward by the sloping side thereof. The reflected laser beam is incident on the apex of the 3-facet reflector 310 through the through hole 343. The refractive index of the prism type second reflector 352 is greater than that of the air, and the laser beam is incident thereon at an angle less than the critical angle for total reflection, so that the incident laser beam is totally reflected. The laser beam reflected downward by the sloping side of the second reflector 352 is incident on the bottom side of the second reflector 352 at a right angle which is greater than the total reflection angle, so that the laser beam is transmitted through the bottom side of the second reflector 352 without reflection.

As described herein, the 6-DOF motion measuring apparatus according to the present invention can easily measure the 6-DOF motion of an object using three PSDs and a 3-facet reflector. The 6-DOF motion measuring apparatus according to the present invention has a simple configuration and can be manufactured at low cost. The 6-DOF motion of an object can be measured by mounting the 3-facet reflector on the object. Thus, although the object is small, its motion can be easily measured. According to the present invention, the laser beam and the object whose motion is to be measured are displaced together, so that the laser beam accurately tracks and enters the apex of the 3-facet reflector, thereby increasing the reliability of measured values. Thus, although the object moves at high speed, its displacement can be easily measured because the 3-facet reflector fixed to the object and the laser source are displaced together.

As described previously, the 2-stage swing arm type optical system for measuring the 6-DOF motion of a HDD slider according to the present invention can accurately measure the 6-DOF motion of the slider when the slider moves along a track and across tracks. For the rapid displacement of the slider which occurs in searching for a track, the 6-DOF displacement can be measured with increased reliability since a laser beam emitted from the laser scanner accurately tracks the motion of the 3-facet reflector fixed to the slider.

While the 6-DOF motion measuring apparatus using a multidirectional reflector and the swing arm type optical system for measuring the 6-DOF motion of a HDD slider according to the present invention have been particularly shown and described with reference to preferred embodiments thereof, it will be understood by those skilled in the art that various changes in form and details may be made therein without departing from the spirit and scope of the invention as defined by the appended claims.

What is claimed is:

1. An apparatus for measuring 6 degree-of-freedom (DOF) motion of an object using a laser beam emitted from a laser source, the apparatus comprising:

a multidirectional reflector having at least three reflecting sides by which the laser beam is slit and reflected in three directions, the multidirectional reflector being provided to the object whose motion is to be measured;

three position-sensitive detectors for receiving three sub-laser beams reflected from the multidirectional reflector; and a controller for calculating the 6-DOF motion of the multidirectional reflector using the intensity distributions of the three sub-laser beams received by the three position sensitive detectors assuming that the laser beam before reflection has a Gaussian intensity distribution.

2. The apparatus of claim 1, wherein the laser beam from the laser source tracks the apex of the multidirectional reflector at which the three reflecting sides meet.

3. The apparatus of claim 1, wherein the laser source can move in two dimensions such that the laser beam emitted from the laser source tracks the apex of the multidirectional reflector at which the three reflecting sides meet.

4. The apparatus of claim 1, wherein the controller receives electric signals from the position-sensitive detectors, and analyzes the intensity distributions of the three sub-laser beams received by the position-sensitive detectors to determine whether or not the intensity distributions of the three sub-light beams are the same.

5. The apparatus of claim 4, wherein the controller adjusts the location of the laser source if the intensity distributions of the three sub-light beams are not the same.

6. A swing arm type optical system using a laser beam emitted from a laser beam scanner to measure 6 degree-of-freedom (DOF) motion of a slider in a hard disc drive (HDD), the swing arm type optical system comprising:

a multidirectional reflector having three reflecting sides on which the laser beam is simultaneously incident, the multidirectional reflector being mounted on or adjacent to the slider, wherein the relative positions of the slider and the multidirectional reflector are fixed;

at least one optical path forming reflector for adjusting the traveling path of the laser beam scanned from the laser beam scanner such that the laser beam is incident on the apex of the multidirectional reflector at which the three reflecting sides meet;

three position-sensitive detectors disposed in the optical paths of three sub-laser beams reflected from the multidirectional reflector;

a controller for measuring the 6-DOF motion of the multidirectional reflector by analyzing the intensity distributions of the three sub-laser beams received by the three position sensitive detectors assuming that the laser beam before reflection has a Gaussian intensity distribution; and a plurality of swing arms which support the slider and along which the traveling path of the laser beam is formed.

7. The swing arm type optical system of claim 6, wherein the rear ends of the plurality of the swing arms are connected to a pivot, and the plurality of swing arms pivot around the pivot.

8. The swing arm type optical system of claim 7, wherein the plurality of swing arms comprise an upper swing arm and a lower swing arm, a through hole is formed at the front end of the upper swing arm, and the laser beam travels along the direction of the upper swing arm and is incident on the apex of the multidirectional reflector through the through hole.

9. The swing arm type optical system of claim 8, wherein the optical path forming reflector comprises a first reflector mounted on the top of the pivot about which the upper and lower swing arms pivot, and a second reflector mounted at the through hole of the upper swing arm; and the laser beam emitted from the laser beam scanner is reflected by the first and second reflectors and is incident on the apex of the multidirectional reflector.

10. The swing arm type optical system of claim 9, wherein the first and second reflectors have a 45-degree sloping side, the 45-degree sloping sides of the first and second reflectors are parallel sloping down toward the front end of the upper swing arm, the laser beam scanned from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

11. The swing arm type optical system of claim 7, wherein the plurality of swing arms comprise an upper swing arm and a lower swing arm, the upper swing arm is formed as a rigid body, the lower swing arm includes a suspension and a flexure which are joined together, and the slider is mount on the bottom of the flexure.

12. The swing arm type optical system of claim 11, wherein the first and second reflectors have a 45-degree sloping side, the 45-degree sloping sides of the first and second reflectors face each other, the laser beam emitted from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

13. The swing arm type optical system of claim 6, wherein the plurality of swing arms comprise an upper swing arm and a lower swing arm, a through hole is formed at the front end of the upper swing arm, and the laser beam travels along the direction of the upper swing arm and is incident on the apex of the multidirectional reflector through the through hole.

14. The swing arm type optical system of claim 13, wherein the optical path forming reflector comprises a first reflector mounted on the top of the pivot about which the upper and lower swing arms pivot, and a second reflector mounted at the through hole of the upper swing arm; and the laser beam emitted from the laser beam scanner is reflected by the first and second reflectors and is incident on the apex of the multidirectional reflector.

15. The swing arm type optical system of claim 14, wherein the first and second reflectors have a 45-degree sloping side, the 45-degree sloping sides of the first and second reflectors are parallel sloping down toward the front end of the upper swing arm, the laser beam scanned from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

16. The swing arm type optical system of claim 6, wherein the plurality of swing arms comprise an upper swing arm and a lower swing arm, the upper swing arm is formed as a rigid body, the lower swing arm includes a suspension and a flexure which are joined together, and the slider is mount on the bottom of the flexure.

17. The swing arm type optical system of claim 16, wherein the first and second reflectors have a 45-degree sloping side, the 45-degree sloping sides of the first and second reflectors face each other, the laser beam emitted from the laser beam scanner is reflected by the 45-degree sloping side of the first reflector toward the 45-degree sloping side of the second reflector, and the laser beam reflected by the 45-degree sloping side of the first reflector is reflected by the 45-degree sloping side of the second reflector such that the reflected laser beam is incident on the apex of the multidirectional reflector through the through hole.

* * * * *